(12) United States Patent
Kossmann et al.

(10) Patent No.: US 6,716,612 B2
(45) Date of Patent: Apr. 6, 2004

(54) DNA MOLECULES CODING FOR DEBRANCHING ENZYMES DERIVED FROM PLANTS

(76) Inventors: Jens Kossmann, Duppelstr. 29, Berlin (DE), 14163; Michael Emmermann, Rehsprung 4, Bergholz Rehbrucke (DE), 14558; Ivar Virgin, Alkulareovagen 19, Stockholm SE-11543 (SE); Andreas Renz, Rathenaustrasse 44, Bayreuth D-95444 (DE)

( * ) Notice: Subject to any disclaimer, the term of this patent is extended or adjusted under 35 U.S.C. 154(b) by 0 days.

(21) Appl. No.: 10/208,349

(22) Filed: Jul. 29, 2002

(65) Prior Publication Data

US 2003/0175931 A1 Sep. 18, 2003

Related U.S. Application Data

(62) Division of application No. 09/573,629, filed on May 17, 2000, now abandoned, which is a division of application No. 08/860,339, filed as application No. PCT/EP95/05091 on Dec. 22, 1995, now Pat. No. 6,117,665.

(30) Foreign Application Priority Data

Dec. 22, 1994 (DE) .......................................... 44 47 387

(51) Int. Cl.[7] ............................ C12N 9/44; C12N 1/20; C12N 15/00; C07H 21/04; A01H 1/00
(52) U.S. Cl. ................. 435/210; 435/252.3; 435/320.1; 435/410; 435/412; 435/417; 536/23.2; 800/278; 800/295
(58) Field of Search ............................ 435/210, 252.3, 435/320.1, 410, 417; 536/23.2, 23.6; 800/278, 295

(56) References Cited

U.S. PATENT DOCUMENTS 4,454,161 A 6/1984 Okada et al. ................. 426/48

FOREIGN PATENT DOCUMENTS

| AU | B-19028/95 | 10/1995 |
|---|---|---|
| EP | 0 479 359 A1 | 4/1992 |
| EP | 0 529 894 A1 | 3/1993 |
| EP | 0 554 122 A1 | 8/1993 |
| WO | WO 92/11382 | 7/1992 |
| WO | WO 92/14827 | 9/1992 |
| WO | WO 95/04826 | 2/1995 |
| WO | WO 95/09922 | 4/1995 |

OTHER PUBLICATIONS

Accession No. X83969 [S. oleracea L. mRNA for pullulanase] and the translated product Q41386 [Renz et al. 1995]; and Sequence alignments with Applicants' SEQ ID NOS : 17 & 18 respectively.*
R.C. Black et al., "Genetic Interactions Affecting Maize Phytoglycogen and the Phytoglycogen–Forming Branching Enzyme", *Genetics*, 53, pp. 661–668 (Apr. 1966).
L. Curtis Hannah et al. "Biotechnological Modification of Carbohydrates for Sweet Corn and Maize Improvement", *Scientia Horticulturae*, 55, pp. 177–197 (1993).
Yukuo Ishizaki et al., "Debranching Enzymes of Potato Tubers (*Solanum tuberosum* L.). I. Purification and Some Properties of Potato Isoamylase", *Agric. Biol. Chem.*, 47(4), pp. 771–779 (1983).
Nobuhiro Katsuragi et al., "Entire Nucleotide Sequence of the Pullulanese Gene of *Klebsiella aerogenes* W70", *Journal of Bacteriology*, 169, pp. 2301–2306 (May 1987).
Bin Li et al., "Characterization and Subcellular Localization of Debranching Enzyme and Endoamylase from Leaves of Sugar Beet", *Plant Physiol.*, 98, pp. 1277–1284 (1992).
Isabella Ludwig et al., "Purification and Properties of Spinach Leaf Debranching Enzyme", *Plant Physiol.*, 74, pp. 856–861 (1984).
D.J. Manners et al., "Studies on Carbohydrate–Metabolising Enzymes: Part XX. Sweet Corn Debranching Enzymes", *Carbohyd. Res.*, 9, pp. 107–121 (1969).
David Pan et al., "A Debranching Enzyme Deficiency in Endosperms of the *Sugary–1* Mutants of Maize", *Plant Physiol.*, 74, pp. 324–328 (1984).
A. Renz et al., "S.oleracea L. mRNA for Pullulanase", EMBL Sequence Database, Accession No. X83969 (Jan. 19, 1995).
Sigma Chemical Company (1993) Catalog Product Numbers –S4251 or S2004 or S2630 or S4501.

* cited by examiner

*Primary Examiner*—T K Saidha
(74) *Attorney, Agent, or Firm*—Fish & Neave; James F. Haley, Jr.; Grant Kalinowski

(57) ABSTRACT

The invention describes DNA molecules which code for plant proteins having the biological activity of a debranching enzyme. Furthermore described are transgenic plant cells and plants having reduced or increased debranching enzyme activity, as well as modified starch isolatable from the cells and plants.

7 Claims, 7 Drawing Sheets

DNA MOLECULES CODING FOR DEBRANCHING ENZYMES DERIVED FROM PLANTS

Figure 1:
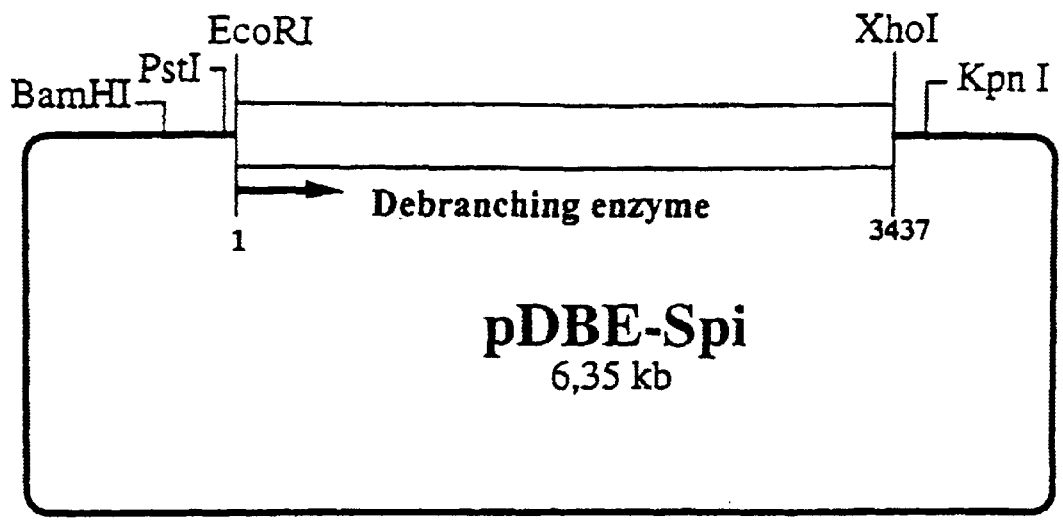

This application is a division of U.S. application Ser. No. 09/573,629, filed May 17, 2000, now abandoned which is a division of U.S. application Ser. No. 08/860,339, filed Nov. 25, 1997, now U.S. Pat. No. 6,117,665, which is a 371 of of PCT/EP95/05091 filed Dec. 22, 1995, the disclosures of which are hereby incorporated by reference in their entireties.

The present invention relates to DNA molecules coding for proteins from plants having the enzymatic activity of a debranching enzyme (R enzyme). The invention furthermore relates to a process for modifying the branching degree of amylopectin synthesized in plants, and to plants and plant cells in which an amylopectin having a modified branching degree is synthesized due to the expression of an additional debranching enzyme activity or the inhibition of an endogenous debranching enzyme activity, as well as to the starch obtainable from said plant cells and plants.

Starch plays an important role both as storage substance in a variety of plants and as reproductive, commercially useful raw material and is gaining significance. For the industrial application of starch it is necessary that the starch meets the requirements of the manufacturing industry in terms of its structure, form and/or other physico-chemical parameters. For the starch to be useful in as many fields of application as possible it is furthermore necessary that it is obtainable in as many forms as possible.

While the polysaccharide starch is composed of chemically uniform components, the glucose molecules, it is a complex mixture of different molecule forms that exhibit differences as regards their polymerization degree and the presence of branches. One distinguishes the amylose starch, an essentially unbranched polymer of $\alpha$-1,4 glycosidically linked glucose molecules from the amylopectin starch, a branched polymer, the branches of which are the result of additional $\alpha$-1,6 glycosidic bonds.

In plants typically used for starch production, such as maize or potato, both starch forms are present in a ratio of about 25 parts of amylose to 75 parts of amylopectin. In addition to amylopectin, maize, for example, exhibits another branched polysaccharide, the so-called phytoglycogen which differs from the amylopectin by a higher branching degree and a differing solubility (see, e.g., Lee et al., Arch. Biochem. Biophys. 143 (1971), 365–374; Pan and Nelson, Plant Physiol. 74 (1984), 324–328). In the present application the term amylopectin is intended to comprise phytoglycogen.

With a view to the uniformity of the basic compound starch for its industrial application starch-producing plants are required that contain, e.g., either only the component amylopectin or only the component amylose. For other applications plants are required that synthesize forms of amylopectin of different degrees of branching.

Such plants can be generated, e.g., by breeding or mutagenesis techniques. It is known of certain plant species, e.g., maize, that mutagenesis can be used to generate varieties producing only amylopectin. For potato, a genotype was generated by chemical mutagenesis for a haploid line that does not produce amylose (Hovenkamp-Hermelink, Theor. Appl. Genet. 75 (1987), 217–221). Haploid lines, however, or the homozygous diploid or tetraploid lines derived thereof are not useful for agricultural purposes. Mutagenesis techniques, however, cannot be applied to the tetraploid lines that are interesting for agriculture since due to the presence of four different genotypes inactivation of all copies of a gene is not technically feasible. Therefore, in the case of potato, one must fall back on other techniques, e.g., the specific genetically engineered modification of plants.

For example it is known from Visser et al. (Mol. Gen. Genet. 225 (1991), 289) and WO 92/11376 that varieties can be generated by anti-sense inhibition of the gene for the starch granule-bound starch synthase in potato that synthesize substantially pure amylopectin starch. WO 92/14827 discloses DNA sequences coding for a branching enzyme (Q enzyme) that introduces $\alpha$-1,6 branches into amylopectin starch. With these DNA sequences it should be possible to generate transgenic plants which exhibit a modified amylose/amylopectin ratio of the starch.

In order to furthermore specifically modify the branching degree of starch synthesized in plants by using genetic engineering it is still necessary to identify DNA sequences coding for enzymes that are involved in starch metabolism, particularly in the branching of starch molecules.

In addition to the Q enzymes that are capable of introducing branches into starch molecules plants comprise enzymes that are capable of dissolving branching. These enzymes are referred to as debranching enzymes and are divided into three groups in terms of their substrate specificity:

(a) Pullulanases that use amylopectin as substrate in addition to pullulan can be found in microorganisms such as Klebsiella and in plants. In plants these enzymes are often referred to as R enzymes.

(b) Isoamylases that do not use pullulan but glycogen and amylopectin as substrate can likewise be found in microorganisms and plants. Isoamylases have been described, e.g., for maize (Manners and Rowe, Carbohydr. Res. 9 (1969), 107) and potato (Ishizaki et al., Agric. Biol. Chem. 47 (1983), 771–779).

(c) Amylo-1,6-glucosidases have been described for mammals and yeasts and use limit dextrins as substrates.

Li et al. (Plant Physiol. 98 (1992), 1277–1284) succeeded in detecting in sugar beet only one debranching enzyme of the pullulanase type in addition to five endoamylases and two exoamylases. Having a size of about 100 kD and a pH optimum of 5.5, this enzyme is localized in the chloroplasts. For spinach, too, a debranching enzyme has been described that uses pullulan as substrate. Both the debranching enzyme of spinach and that of sugar beet possess an activity that is lower by a factor of 5 when reacting it with amylopectin as substrate instead of pullulan as substrate (Ludwig et al., Plant Physiol. 74 (1984), 856–861; Li et al., Plant Physiol. 98 (1992), 1277–1284).

The activity of a debranching enzyme was examined by Hobson et al. (J. Chem. Soc. (1951), 1451) for potato which is a starch-storing cultivated plan[+] that is important from the agricultural point of view. They succeeded in proving that the corresponding enzyme—in contrast to the Q enzyme—does not possess chain-extending activity but merely hydrolyzes $\alpha$-1,6 glycosidic bonds. However, it has not been possible so far to characterize the enzyme in more detail. For potato processes for the purification of the debranching enzyme as well as partial peptide sequences of the purified protein have been proposed (German patent application P 43 27 165.0 and PCT/EP94/026239). In principle, it should be possible to identify DNA molecules coding for the respective proteins by means of known peptide sequences when using degenerate oligonucleotide probes. However, in practice, often the problem arose that the degree of degeneration of the probe is too high or the probes are too short to specifically identify sequences coding for the desired protein.

Despite the knowledge of the proposed peptide sequences of the debranching enzyme of potato researchers so far have not been able to isolate DNA molecules coding for debranching enzymes of plants by hybridization to degenerate oligonucleotides or by other genetic or immunological approaches such as proposed in German patent application P 43 27 165.0.

For spinach, too, for which the purification of the debranching enzyme has been described by Ludwig et al. (Plant Physiol. 74 (1984), 856–861), researchers have not been able to either determine peptide sequences or to identify DNA molecules coding for said protein.

The problem underlying the present invention is therefore to provide DNA molecules coding for proteins of plants having the enzymatic activity of a debranching enzyme and allowing to generate transgenic plant cells and plants having an increased or reduced activity of a debranching enzyme.

The problem is solved by the provision of the embodiments described in the claims.

The present invention therefore relates to DNA molecules coding for proteins of plants having the biological activity of a debranching enzyme, or a biologically active fragment thereof.

Such a DNA molecule preferably codes for a debranching enzyme of plants comprising the amino acid sequence indicated in Seq ID No. 18 or Seq ID No. 24. More preferably, such a DNA molecule comprises the nucleotide sequence indicated in Seq ID No. 17 or Seq ID No. 23, particularly the coding region thereof.

The subject matter of the invention are also DNA molecules coding for proteins of plants having the biological activity of a debranching enzyme, or biologically active fragments thereof and that hybridize to any of the DNA molecules described above.

The term "hybridization" in this context means hybridization under conventional hybridization conditions, preferably under stringent conditions such as described by, e.g. Sambrook et al. (1989, Molecular Cloning, A Laboratory Manual, 2nd Edition, Cold Spring Harbor Laboratory Press, Cold Spring Harbor, N.Y.). These DNA molecules that hybridize to the DNA molecules according to the present invention in principle can be derived from any plant possessing such DNA molecules. Preferably, they are derived from monocotyledonous or dicotyledonous plants, preferably from useful plants, and most preferably from starch-storing plants.

DNA molecules hybridizing to the DNA molecules of the present invention can be isolated, e.g, from genomic libraries or cDNA libraries of various plants.

Such DNA molecules from plants can be identified and isolated by using the DNA molecules of the present invention or fragments of these DNA molecules or the reverse complements of these molecules, e.g., by hybridization according to standard techniques (see, e.g., Sambrook et al., 1989, Molecular Cloning, A Laboratory Manual, 2nd Edition, Cold Spring Harbor Laboratory Press, Cold Spring Harbor, N.Y.).

As hybridization probe, e.g., DNA molecules can be used that have exactly or substantially the same DNA sequence indicated in Seq ID No. 17 or Seq ID No. 23 or fragments of said sequence. The DNA fragments used as hybridization probes can also be synthetic DNA fragments obtained by conventional DNA synthesis techniques and the sequence of which is substantially identical to that of the DNA molecules according to the invention. Once genes hybridizing to the DNA molecules of the invention have been identified and isolated it is necessary to determine the sequence and to analyze the properties of the proteins coded for by said sequence.

The term "hybridizing DNA molecules" includes fragments, derivatives and allelic variants of the above-described DNA molecules that code for the above-described protein or a biologically active fragment thereof. Fragments are understood to be parts of DNA molecules long enough to code for the described protein or a biologically active fragment thereof. The term "derivative" means in this context that the DNA sequences of these molecules differ from the sequences of the above-described DNA molecules in one or more positions and are highly homologous to said DNA sequence. Homology is understood to refer to a sequence identity of at least 40%, particularly an identity of at least 60%, preferably more than 80% and still more preferably more than 90%. The deviations from the DNA molecules described above can be the result of deletion, substitution, insertion, addition or recombination.

Homology furthermore means that the respective DNA sequences or encoded proteins are functionally and/or structurally equivalent. The DNA molecules that are homologous to the DNA molecules described above and that are derivatives of said DNA molecules are regularly variations of said DNA molecules which represent modifications having the same biological function. They may be naturally occurring variations, such as sequences of other plant species, or mutations. These mutations may occur naturally or may be achieved by specific mutagenesis. Furthermore, these variations may be synthetically produced sequences.

The allelic variants may be naturally occurring variants as well as synthetically produced or genetically engineered variants.

The proteins encoded by the various variants of the DNA molecules of the invention share specific common characteristics, such as enzymatic activity, molecular weight, immunological reactivity, conformation, etc., as well as physical properties, such as electrophoretic mobility, chromatographic behavior, sedimentation coefficients, solubility, spectroscopic properties, stability, pH optimum, temperature optimum, etc.

Enzymatic activity of the debranching enzyme can be detected in a iodine stain test such as described in Example 5. This test is based on the finding that a protein having a starch-modifying activity can be detected by separating protein extracts, e.g., from tubers, in non-denaturing amylopectin-containing polyacrylamide gels (PAAG) and subsequently staining the gel, after incubation in a suitable buffer, with iodine. While unbranched amylose forms a blue complex with iodine, amylopectin results in a reddish-purple color. Amylopectin-containing polyacrylamide gels giving a reddish-purple color when reacted with iodine result in a change of color up to a blue color of the gel at places where the debranching activity is localized, since the branches of the purple-staining amylopectin are digested by the debranching enzyme.

Alternatively, debranching enzyme activity can be detected by the DNSS test (see Ludwig et al., Plant Physiol. 74 (1984), 856–861).

The present invention furthermore relates to DNA molecules the sequences of which differ from the sequences of the above-identified DNA molecules due to degeneracy of the genetic code, and which code for a protein of a plant having the biological activity of a debranching enzyme or for a biologically active fragment thereof.

According to a preferred embodiment the protein coded for by the DNA molecules according to the invention contains at least one of the peptide sequences depicted in Seq ID No. 1 to Seq ID No. 14.

According to another preferred embodiment the debranching enzymes of plants coded for by the DNA molecules of the invention can be isolated from plant protein extracts by fractionated ammonium sulfate precipitation and subsequent affinity chromatography on β-cyclodextrin.

Preferably, the DNA molecules of the invention code for proteins that exhibit a molecular weight between 50 and 150 kD in SDS gel electrophoresis, preferably between 70 and 130 kD, and most preferably between 90 and 110 kD.

In principle, the DNA molecules according to the invention can be derived from any plant organism that expresses the proteins described, preferably from taxonomically higher plants, particularly from monocotyledonous or dicotyledonous plants, preferably from plants that synthesize or store starch. Most preferred are, e.g., cereals (such as barley, rye, oat, wheat, etc.), maize, rice, pea, cassava, etc.

According to a preferred embodiment the DNA molecules of the invention are derived from plants of the family Solanaceae or from plants of the family Chenopodiaceae, preferably from *Solanum tuberosum* or *Spinacia oleracea*.

The invention furthermore relates to vectors, particularly plasmids, cosmids, viruses, bacteriophages and other vectors conventional in genetic engineering that contain the above-described DNA molecules of the invention.

According to a preferred embodiment the DNA molecules contained in the vectors are linked to regulatory DNA sequences allowing transcription and translation in procaryotic or eucaryotic cells.

According to another embodiment the invention relates to host cells, particularly procaryotic or eucaryotic cells that have been transformed with a DNA molecule or a vector described above, and cells that are derived from such host cells.

Furthermore, the present invention relates to processes for producing a protein of a plant having the biological activity of a debranching enzyme or a biologically active fragment thereof, wherein host cells according to the invention are cultivated under suitable conditions and the protein is obtained from the culture.

Another subject matter of the invention are the proteins obtainable by said process.

The invention furthermore relates to proteins of plants having the biological activity of a debranching enzyme that are coded for by the DNA molecules of the invention, except for the proteins obtained from spinach and potato that have already been described.

By providing the DNA molecules of the invention it is possible to genetically engineer plant cells such that they exhibit an increased or reduced debranching enzyme activity as compared to wild type cells. Such a modified starch is suitable for various purposes.

According to a preferred embodiment the host cells of the invention are transgenic plant cells that exhibit an increased debranching enzyme activity as compared to non-transformed cells due to the presence and expression of an additionally introduced DNA molecule of the invention.

Another subject matter of the invention are transgenic plants containing the transgenic plant cells described above.

The invention furthermore relates to the starch obtainable from the transgenic plant cells or plants. Due to the increased debranching enzyme activity the amylopectin starch synthesized by the transgenic cells or plants has properties differing from those of starch from non-transformed plants. For example, when analyzing the viscosity of aqueous solutions of this starch upon treating they display a maximum viscosity lower than that of starch of non-transformed plants. Preferably the value of the maximum viscosity is reduced by at least 40%, particularly by at least 55% and still more preferably by at least 65% in comparison with the maximum viscosity of starch from wild type plants. Furthermore, the final viscosity of aqueous solutions of the modified starch after cooling is higher than that of wild type starch. Preferably, the final viscosity is at least 10% higher, particularly at least 30% and still more preferably at least 50% higher than that of starch form wild type plants.

Moreover, the stability of gels consisting of the modified starch is higher than that of gels of wild type starch. The force that is required to deform gels of the modified starch is greater by a factor of at least 2.5, particularly of at least 3.5 and still more preferably of at least 5.5 than that required to deform gels of wild type starch. Furthermore, the phosphate content of the modified starch is comparable to that of wild type starch.

Another object of the invention is the use of the described starch for the production of food and industrial products.

Another subject matter of the invention is propagating material of the plants of the invention, such as seeds, fruit, cuttings, tubers, root stocks, etc., with this propagating material containing transgenic plant cells described above.

The present invention furthermore relates to transgenic plant cells in which the activity of the debranching enzyme is reduced due to the inhibition of the transcription or translation of endogenous nucleic acid molecules coding for a debranching enzyme. This is preferably achieved by expressing a DNA molecule of the invention in the respective plant cells in antisense direction. Due to an antisense effect the debranching enzyme activity is reduced. Another possibility of reducing the debranching enzyme activity in plant cells is to express suitable ribozymes that specifically cleave transcripts of the DNA molecules of the invention. The production of such ribozymes using the DNA molecules of the invention is known in the art. Alternatively, the debranching enzyme activity in the plant cells may be reduced by a co-suppression effect.

The invention furthermore relates to transgenic plants containing the transgenic plant cells described above having reduced debranching enzyme activity. Another subject matter of the invention is the modified starch obtainable from the transgenic cells or plants. The amylopectin starch of the transgenic cells and plants exhibits an altered branching degree as compared to the starch of non-transformed plants due to the reduced debranching enzyme activity. Furthermore, the modified starch obtainable from the described transgenic plants may differ in several aspects form starch of wild type plants. For example, when analyzing the viscosity of aqueous solutions of this starch upon heating they display a maximum viscosity that is lower than that of starch from non-transformed plants. Preferably, the value of the maximum viscosity is reduced by at least 35%, particularly by at least 40% and still more preferably by at least 50% in comparison to the maximum viscosity of starch from wild type plants.

Starch granules of the modified starch synthesized by plants with reduced debranching enzyme activity may have a rough, chapped or even frayed surface.

Furthermore, the modified starch is characterized in that gels produced from this starch are more stable than gels of wild type starch. The force that is required to deform gels of the modified starch is greater by a factor of at least 2.3, more preferably by at least 3.8 and still more preferably by at least 6.0 than that required to deform gels of wild type starch.

The phosphate content of the modified starch is preferably higher than that of wild type starch. The increase in phosphate content depends on the degree of reduction of the debranching enzyme activity. Preferably, the phosphate content is at least 15%, more preferably at least 25% and still more preferably at least 60% higher than that of wild type starch.

Still another object of the invention is the use of the described starch for the production of food or industrial products.

The invention also relates to propagating material of the above-described transgenic plants, such as seeds, fruit, cuttings, tubers, root stocks, etc., with the propagating material containing above-described transgenic plant cells.

Transgenic plant cells that due to the additional expression of a debranching enzyme generate an amylopectin starch having an altered branching degree as compared to the amylopectin starch synthesized by wild type plants are obtainable, e.g., by a process comprising the following steps:
(a) Producing an expression cassette comprising the following DNA sequences:
 (i) a promoter allowing transcription in plant cells;
 (ii) at least one DNA sequence coding for a protein having the enzymatic activity of a debranching enzyme and being fused to the 3' end of the promoter in sense orientation; and
 (iii) optionally a termination signal for the transcription termination and the addition of a poly-A tail to the transcript formed that is coupled to the 3' end of the coding region; and
(b) transformation of plant cells with the expression cassette produced in step (a).

Transgenic plant cells that due to the reduction of the activity of a debranching enzyme generate an amylopectin starch having an altered branching degree as compared to the amylopectin starch synthesized by wild type plants are obtainable, e.g., by a process comprising the following steps:
(a) Producing an expression cassette comprising the following DNA sequences:
 (i) a promoter allowing transcription in plant cells;
 (ii) at least one DNA sequence coding for a protein having the enzymatic activity of a debranching enzyme or at least part of such a protein and being fused to the 3' end of the promoter in anti-sense orientation; and
 (iii) optionally a termination signal for the transcription termination and the addition of a poly-A tail to the transcript formed that is coupled to the 3' end of the DNA sequence defined in (ii); and
(b) transformation of plant cells with the expression cassette produced in step (a).

In principle, any promoter that is functional in plants can be used as the promoter mentioned in (i). The promoter may be homologous or heterologous with respect to the plant species used. A suitable promoter is, e.g., the 35S promoter of the cauliflower mosaic virus (Odell et al., Nature 313 (1985), 810–812) which allows constitutive expression in all tissues of a plant, and the promoter construct described in WO94/01571. However, promoters can be used that lead to expression of subsequent sequences only at a certain point of time determined by external factors (see, e.g., WO93/07279) or in a certain tissue of the plant (see, e.g., Stockhaus et al., EMBO J. 8 (1989), 2245–2251). Preferably promoters are used that are active in the starch-storing organs of the plants to be transformed. These starch-storing organs are, e.g., the maize grains in maize while it is the tubers in potato. For the transformation of potato, the tuber-specific B33 promoter (Rocha-Sosa et al., EMBO J. 8 (1989), 23–29) is particularly, but not exclusively, useful. Provided that the DNA sequence mentioned under process step (a)(ii) coding for a protein having the enzymatic activity of a debranching enzyme is linked to the promoter in sense orientation, this DNA sequence can be of native or homologous origin or of foreign or heterologous origin with respect to the plant species to be transformed.

The use of the DNA molecules of the invention is preferred. In principle, the synthesized protein can be localized in any compartment of the plant cell. Debranching enzymes of plants are regularly localized in the plastids and therefore possess a signal sequence for the translocation in these compartments. In the case of the amino acid sequence depicted in Seq ID No. 17 the signal sequence consists of the 64 N-terminal amino acids. In order to achieve localization in another compartment of the cell, the DNA sequence coding for said signal sequence must be removed and the coding region must be linked to DNA sequences allowing localization in the respective compartment. Such sequences are known (see, e.g., Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

Provided that the DNA sequence mentioned under process step (a) (ii) coding for a protein having the enzymatic activity of a debranching enzyme is linked to the promoter in anti-sense orientation, this DNA sequence preferably is of homologous origin with respect to the plant species to be transformed. However, DNA sequences can also be used that exhibit a high degree of homology to endogenous present debranching enzyme genes, particularly homologies over 80%, preferably homologies between 90% and 100% and most preferably homologies over 95%.

Sequences down to a minimum length of 15 bp can be used. An inhibiting effect, however, cannot be excluded even if shorter sequences are used. Preferred are longer sequences between 100 and 500 base pairs; for an efficient anti-sense inhibition sequences with a length of more than 500 base pairs are particularly used. Usually, sequences are used that are shorter than 5000 base pairs, preferably sequences that are shorter than 2500 base pairs.

In the case of the transformation of potato the DNA sequence preferably is the DNA sequence depicted in Seq ID No. 23 or parts thereof that are long enough to produce an anti-sense effect.

Termination signals for the transcription in plant cells have been described and can be freely interchanged. For example, the termination sequence of the octopin synthase gene from *Agrobacterium tumefaciens* can be used.

The transfer of the expression cassette constructed according to process step (a) to plant cells is preferably brought about by using plasmids, particularly plasmids that allow stable integration of the expression cassette into the plant genome.

In principle, the processes described above can be applied to all plant species. Of interest are both monocotyledonous and dicotyledonous plants. For various monocotyledonous and dicotyledonous plant species transformation techniques have already been described. The processes are preferably applied to useful plants, in particular starch-producing plants, such as cereals (such as maize, wheat, barley, rye, oat), potato, pea, rice, cassava, etc.

For the preparation of the introduction of foreign genes into taxonomically higher plants there is a wide choice of cloning vectors that contain a replication signal for *E. coli* and a marker gene for the selection of transformed bacterial cells. Examples of such vectors are pBR322, pUC series, M13mp series, pACYC184, etc. The desired sequence can be introduced into the vector at a suitable restriction site. The plasmid obtained is used to transform *E. coli* cells. Transformed *E. coli* cells are cultivated in a suitable medium, harvested and lysed. The plasmid is recovered according to standard techniques. As methods for the analysis for the characterization of the obtained plasmid DNA restriction analyses and sequence analyses are generally used. After each manipulation the plasmid DNA can be cleaved and the resulting DNA fragments can be linked to other DNA sequences.

There is a large number of techniques available for the introduction of DNA into a plant host cell. These techniques include the transformation of plant cells with T-DNA using *Agrobacterium tumefaciens* or *Agrobacterium rhizogenes* as transformant, the fusion of protoplasts, injection, electroporation of DNA, the introduction of DNA via the biolistic technique and other possible techniques.

In the case of injection and electroporation of DNA into plant cells no specific requirements are made to the plasmids used. Simple plasmids such as pUC derivatives can be used. If, however, one intends to regenerate whole plants from the respectively transformed cells, it is necessary that a selectable marker gene is present.

Depending on the method of introduction of the desired genes into the plant cell further DNA sequences can be necessary. If, e.g., the Ti or Ri plasmid is used to transform the plant cell, at least the right border, often, however, the right and left border of the Ti and Ri plasmid T-DNA must be linked as flanking region to the genes to be introduced.

If Agrobacteria are used for transformation, the DNA to be introduced must be cloned into special plasmids, either into an intermediate vector or into a binary vector. The intermediate vectors can be integrated by homologous recombination into the Ti or Ri plasmid of the Agrobacteria due to sequences that are homologous to sequences in the T-DNA. Said plasmid contains the vir region necessary for the transfer of the T-DNA. Intermediate vectors are not able to replicate in Agrobacteria. The intermediate vector can be transferred to *Agrobacterium tumefaciens* using a helper plasmid (conjugation). Binary vectors are able to replicate both in *E. coil* and in Agrobacteria. They contain a selection marker gene and a linker or polylinker flanked by the right and left T-DNA border regions. They can be directly transformed into Agrobacteria (Holsters et al., Mol. Gen. Genet. 163 (1978), 181–187). The plasmids used for transformation of Agrobacteria contain furthermore a selection marker gene allowing selection of transformed bacteria, such as the NPTII gene. The Agrobacterium serving as host cell should contain a plasmid carrying a vir region.

The vir region is necessary for the transfer of the T-DNA to the plant cell. Additional T-DNA may be present. The Agrobacterium so transformed is used to transform plant cells.

The use of T-DNA for the transformation of plant cells has been extensively examined and is sufficiently described in EP 120516; Hoekema, In: The Binary Plant Vector System, Offsetdrukkerij Kanters B. V., Alblasserdam, Chapter V; Fraley et al., Crit. Rev. Plant. Sci., 4:1–46 and An et al., EMBO J. 4 (1985), 277–287. Some binary vectors are already commercially available, e.g., pBIN19 (Clontech Laboratories, Inc. USA).

For the transfer of the DNA to the plant cells plant explants can expediently be cocultivated with *Agrobacterium tumefaciens* or *Agrobacterium rhizogenes*. From the infected plant material (e.g., pieces of leaves, stem segments, roots but also protoplasts or suspension-cultivated plant cells) whole plants can be regenerated on an appropriate medium which may contain antibiotics or biocides for the selection of transformed cells. The plants thus obtained can be screened for the presence of the introduced DNA.

Once the introduced DNA is integrated into the genome of the plant cell, it generally remains there stably and can also be found in the successors of the originally transformed cell. Normally it contains a selection marker which imparts to the transformed plant cells resistance to a biocide or an antibiotic such as kanamycin, G 418, bleomycin, hygromycin or phosphinotricin etc. The selected marker should therefore allow for the selection of transformed cells over cells lacking the introduced DNA.

The transformed cells grow within the cell as usual (cf., e.g., McCormick et al., Plant Cell Reports 5 (1986), 81–84). These plants can be grown in the usual manner and can be cross-bred with plants possessing the same transformed genetic material or other genetic materials. The resulting hybrid individuals have the corresponding phenotypic properties.

Two or more generations should be cultivated in order to make sure that the phenotypic features are stably retained and inherited. Furthermore, seeds should be harvested in order to make sure that the corresponding phenotype or other characteristics have been retained.

The introduction of an expression cassette constructed according to the processes described above results in the formation of RNA in the transformed plant cells. If the DNA sequence coding for a debranching enzyme is linked with the promoter in sense orientation in the expression cassette, mRNA is synthesized which may serve as template for the synthesis of an additional or new debranching enzyme in the plant cells. As a result, these cells exhibit an increased debranching enzyme activity leading to a change of the branching degree of the amylopectin produced in the cells. By this change a starch becomes available that excels vis-á-vis the naturally occurring starch by a more coordinate spatial structure and a higher uniformity. This has inter alia favorable effects on the film-forming properties of the starch.

If the DNA sequence coding for a debranching enzyme is linked with the promoter in anti-sense orientation, an anti-sense RNA is synthesized in transgenic plant cells that inhibits the expression of endogenous debranching enzyme genes. As a result, these cells exhibit a reduced debranching enzyme activity leading to the formation of a modified starch. By using this anti-sense technique it is possible to produce plants in which the expression of endogenous debranching enzyme genes is inhibited in various degrees in a range of 0% to 100%, thereby allowing the production of plants synthesizing amylopectin starch in modified branching degrees. This represents an advantage vis-á-vis conventional breeding and mutagenesis techniques which involve a considerable amount of time and money to provide such a variety. Highly branched amylopectin has a particularly large surface and is therefore specifically suitable as copolymer. A high branching degree furthermore results in an improved solubility in water of the amylopectin. This property is very advantageous for certain technical applications. Particularly suitable for the production of modified amylopectin using the DNA molecules of the invention which code for debranching enzymes is the potato. However, the use of the invention is not limited to this plant species.

The modified starch synthesized in the transgenic plants can be isolated from the plants or plant cells according to conventional methods and can be used for the production of food and industrial products once it is purified.

Due to its properties, the starch obtainable from the plant cells and/or plants of this invention is suitable for various industrial applications.

Basically, starch can be subdivided into two major categories, namely hydrolysis products of starch and what are called native starches. Hydrolysis products essentially include glucose obtained by enzymatic or chemical processes as well as glucose building blocks which can be used for further processes, such as fermentation, or further chemical modifications. In this context, it might be of importance that the hydrolysis process can be carried out simply and inexpensively, currently, it is craried out substantially enzymatically using amyloglucosidase. It is thinkable that costs may be reduced by using lower amounts of enzymes for hydrolysis due to changes in the starch structure, e.g. increase of surface of the grain, improved digestability due to less branching or steric structure, which limits the accessibility for the used enzymes.

The use of what are called native starches, which are used because of their polymer structure, can be subdivided into two large areas:

(a) Use in Foodstuffs

Starch is a classic additive for various foodstuffs, in which it essentially serves the purpose of binding aqueous additives and/or causes an increased viscosity or an increased gel formation. Important characteristic properties are flowing and sorption behavior, swelling and pastification temperature, viscosity and thickening performance, solubility of the starch, transparency and paste structure, heat, shear and acid resistance, tendency to retrogradation, capability of film formation, resistance to freezing/thawing, digestibility as well as the capability of complex formation with e.g. inorganic or organic ions.

(b) Use in Non-Foodstuffs

The other major field of application is in the use of starch as an adjuvant in various production processes and/or as an additive in technical products. The major fields of application for the use of starch as an adjuvant are, first of all, the paper and cardboard industries. In this field, the starch is mainly used for retention (holding back solids), for sizing filler and fine particles, as solidifying substance and for dehydration. In addition, the advantageous properties of starch with regard to stiffness, hardness, sound, grip, gloss, smoothness, tear strength as well as the surfaces are utilized.

Within the paper production process, a differentiation can be made between four fields of application, namely surface, coating, mass and spraying.

The requirements on starch with regard to surface treatment are essentially a high degree of brightness, corresponding viscosity, high viscosity stability, good film formation as well as low formation of dust. When used in coating, the solid content, a corresponding viscosity, a high capability to bind as well as a high pigment affinity are important. As an additive to the mass, rapid, uniform, loss-free dispersion, high mechanical stability and complete retention in the paper pulp are of importance. When using the starch in spraying, corresponding content of solids, high viscosity as well as high capability to bind are also of importance.

A major field of application is, for instance, in the adhesive industry, where the fields of application are subdivided into four areas: the use as pure starch glue, the use in starch glues prepared with special chemicals, the use of starch as an additive to synthetic resins and polymer dispersions as well as the use of starches as extenders for synthetic adhesives. 90% of all starch-based adhesives are used in the production of corrugated board, paper sacks, bags, composite materials for paper and aluminum, boxes and wetting glue for envelopes, stamps, etc.

Another possible use as adjuvant and additive is in the production of textiles and textile care products. Within the textile industry, a differentiation can be made between the following four fields of application: the use of starch as a sizing agent, i.e. as an adjuvant for smoothing and strengthening the burring behavior for the protection against tensile forces active in weaving as well as for the increase of wear resistance during weaving, as an agent for textile improvement mainly after quality-deteriorating pretreatments, such as bleaching, dying, etc., as thickener in the production of dye pastes for the prevention of dye diffusion and as an additive for warping agents for sewing yarns.

Furthermore, the starch may be used as an additive in building materials. One example is the production of gypsum plaster boards, in the course of which the starch mixed in the thin plaster pastifies with the water, diffuses at the surface of the gypsum board and thus binds the cardboard to the board. Other fields of application are admixing it to plaster and mineral fibers. In ready-mixed concrete, starch may be used for the deceleration of the sizing process.

Furthermore, the starch is advantageous for the production of means for ground stabilisation used for the temporary protection of ground particles against water in artificial earth shifting. According to state-of-the-art knowledge, combination products consisting of starch and polymer emulsions can be considered to have the same erosion- and incrustation-reducing effect as the products used so far; however, they are considerably less expensive.

Furthermore, the starch may be used in plant protectives for the modification of the specific properties of these preparations. For instance, starches are used for improving the wetting of plant protectives and fertilizers, for the dosed release of the active ingredients, for the conversion of liquid, volatile and/or odorous active ingredients into microcristalline, stable, deformable substances, for mixing incompatible compositions and for the prolongation of the duration of the effect due to a reduced disintegration.

Another important field of application lies in the fields of drugs, medicine and the cosmetics industry. In the pharmaceutical industry, the starch may be used as a binder for tablets or for the dilution of the binder in capsules. Furthermore, starch is suitable as disintegrant for tablets since, upon swallowing, it absorbs fluid and after a short time it swells so much that the active ingredient is released. Medicinal flowance and dusting powders are further fields of application. In the field of cosmetics, the starch may for example be used as a carrier of powder additives, such as scents and salicylic acid. A relatively extensive field of application for the starch is toothpaste.

Also the use of starch as an additive to coal and briquettes is thinkable. By adding starch, coal can be quantitatively agglomerated and/or briquetted in high quality, thus preventing premature disintegration of the briquettes. Barbecue coal contains between 4 and 6% added starch, calorated coal between 0,1 and 0,5%.

Furthermore, the starch is suitable as a binding agent since adding it to coal and briquette can considerably reduce the emission of toxic substances.

Furthermore, the starch may be used as a flocculent in the processing of ore and coal slurry.

Another field of application is the use as an additive to process materials in casting. For various casting processes, cores produced from sands mixed with binding agents are needed. Nowadays, the most commonly used binding agent is bentonite with modified starches, mostly swelling starches, mixed in.

The purpose of adding starch is increased flow resistance as well as improved binding strength.

Moreover, swelling starches may fulfil more prerequisites for the production process, such as dispersability in cold water, rehydratisability, good mixability in sand and high capability of binding water. In the rubber industry, the starch may be used for improving the technical and optical quality. Reasons for this are improved surface gloss, grip and appearance. For this purpose, the starch is dispersed on the sticky rubberized surfaces of rubber substances before the cold vulcanisation. It may also be used for improving the printability of rubber.

Another field of application for the modified starch is the production of leather substitutes.

In the plastics market, the following fields of application are emerging: the integration of products derived from starch into the processing process (starch is only a filler, there is no direct bond between synthetic polymer and starch) or, alternatively, the integration of products derived from starch into the production of polymers (starch and polymer form a stable bond).

The use of the starch as a pure filler cannot compete with other substances such as talcum. This situation is different when the specific starch properties become effective and the property profile of the end products is thus clearly changed. One example is the use of starch products in the processing of thermoplastic materials, such as polyethylene. In this process, starch and synthetic polymer are combined in a ratio of 1:1 by means of coexpression to form a 'master batch', from which various products are produced by means of common techniques using granulated polyethylene. The integration of starch in polyethylene films may cause an increased substance permeability in hollow bodies, improved water vapor permeability, improved antistatic behavior, improved anti-block behavior as well as improved printability with aqueous dyes.

Another possibility is the use of the starch in polyurethane foams. Due to the adaptation of starch derivatives as well as due to the optimisation of processing techniques, it is possible to control the reaction between synthetic polymers and the starch's hydroxy groups. The result are polyurethane films having the following property profiles due to the use of starch: a reduced coefficient of thermal expansion, decreased shrinking behavior, improved pressure/tension behavior, increased water vapor permeability without a change in water acceptance, reduced flammability and cracking density, no drop off of combustible parts, no halides and reduced aging. Disadvantages that presently still exist are reduced resistance to pressure and to impact.

Product development of film is not the only option. Also solid plastics products, such as pots, plates and bowls can be produced having a starch content of more than 50%. Furthermore, the starch/polymer mixtures offer the advantage that they are much easier biodegradable.

Furthermore, due to their extreme capability to bind water, starch graft polymers have gained utmost importance. These are products having a backbone of starch and a side lattice of a synthetic monomer grafted on according to the principle of radical chain mechanism. The starch graft polymers available today are characterized by an improved binding and retaining capability of up to 1000 g water per g starch at a high viscosity. These super absorbers are used mainly in the hygiene field, e.g. in products such as diapers and sheets, as well as in the agricultural sector, e.g. in seed pellets.

What is decisive for the use of the new starch modified by genetic engineering are, on the one hand, structure, water content, protein content, lipid content, fiber content, ashes/phosphate content, amylose/amylopectin ratio, distribution of the relative molar mass, degree of branching, granule size and form as well as crystallisation, and on the other hand, the properties resulting in the following features: flow and sorption behavior, pastification temperature, thickening performance, solubility, paste structure, transparency, heat, shear and acid resistance, tendency to retrogradation, capability of gel formation, resistance to freezing/thawing, capability of complex formation, iodine binding, film formation, adhesive strength, enzyme stability, digestibility and reactivity. Furthermore, viscosity is particularly pointed out.

Furthermore, the modified starch obtainable from the plant cells and/or plants of this invention may be subjected to further chemical modification, which will result in further improvement of the quality for certain of the above-described fields of application or in a new field of application. These chemical modifications are principally known to the person skilled in the art. These are particularly modifications by means of acid treatment oxidation esterification (formation of phosphate, nitrate, sulfate, xanthate, acetate and citrate starches; other organic acids may also be used for the esterification)

formation of starch ethers (starch alkyl ether, O-allyl ether, hydroxylalkyl ether, O-carboxylmethyl ether, N-containing starch ethers, S-containing starch ethers)

formation of branched starches formation of starch graft polymers.

The invention furthermore relates to the use of the DNA molecules of the invention for the production of plants synthesizing an amylopectin starch having a modified branching degree as compared to that of wild type plants.

A further subject matter of the present invention is the use of the DNA molecules of the invention or of parts of these DNA molecules or of the reverse complements of these molecules for the identification and isolation of homologous molecules coding for proteins having the enzymatic activity of a debranching enzyme, or of fragments of such proteins, from plants or other organisms. For a definition of the term "homology" see above.

FIG. 1 shows plasmid pDBE-Spi

The thin line corresponds to the sequence of pBluescriptSKII(−). The thick line represents the cDNA coding for the debranching enzyme of *Spinacia oleracea*. The cDNA insert is ligated between the EcoRI and XhoI restriction sites of the polylinker of the plasmid. The arrow indicates the orientation of the coding region for the debranching enzyme. The DNA sequence of the cDNA insert is indicated in Seq ID No. 17.

Figure 2:
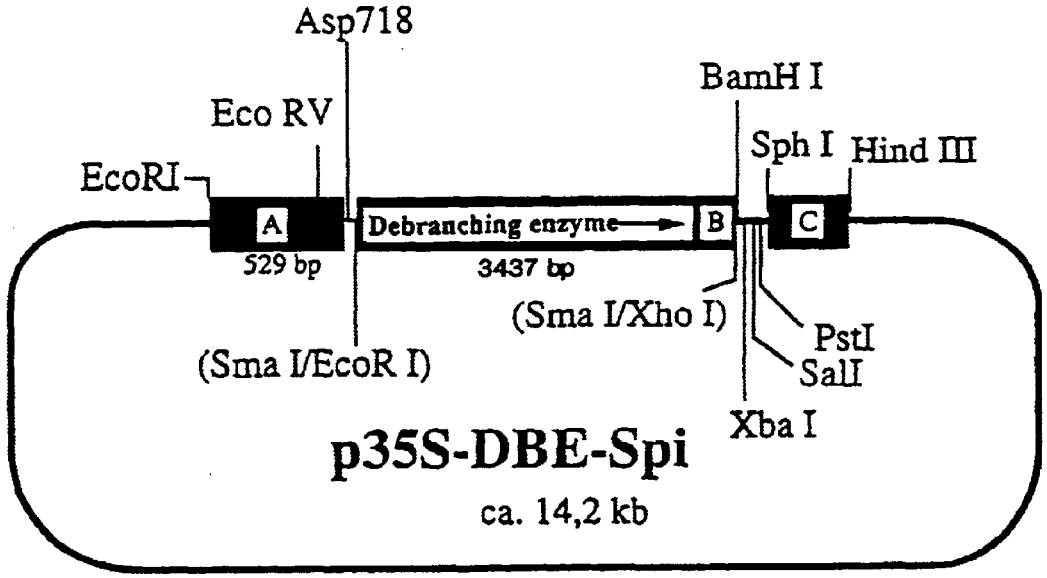

FIG. 2 shows plasmid p35S-DBE-Spi

A=fragment A: CaMV 35S promoter, nt 6909–7437 (Franck et al, Cell 21 (1980), 285–294)

B=fragment B: cDNA from *Spinacia oleracea* coding for the debranching enzyme;

EcoRI/XhoI fragment from pDBE-Spi, about 3440 bp; orientation towards the promoter: sense C=fragment C: nt 11748–11939 of the T-DNA of the Ti plasmid pTiACH5 (Gielen et al., EMBO J. 3 (1984), 835–846)

Figure 3:
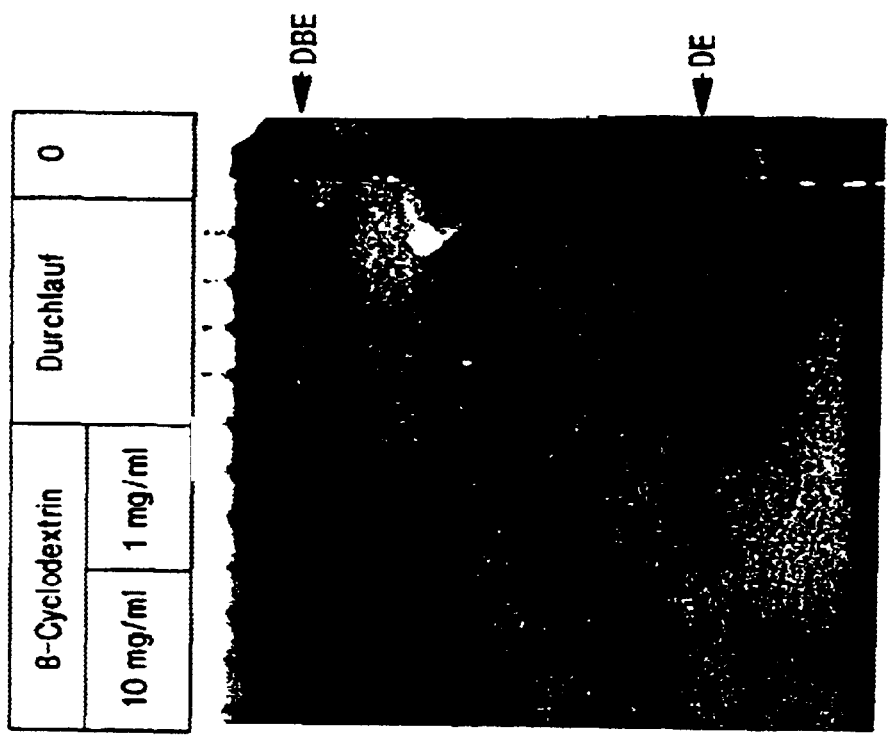

FIG. 3 shows the purification of the debranching enzyme from *Solanum tuberosum*.

0=protein extract of a homogenate from tuber tissue of *Solanum tuberosum*

Durchlauf=void volume of an affinity chromatography of the protein extract on immobilized β-cyclodextrin β-cyclodextrin=elution of the affinity chromatography with dissolved β-cyclodextrin in a concentration of 1 mg/ml or 10 mg/ml DBE=debranching enzyme from *Solanum tuberosum*
DE=disproportionating enzyme from *Solanum tuberosum*

Figure 4:
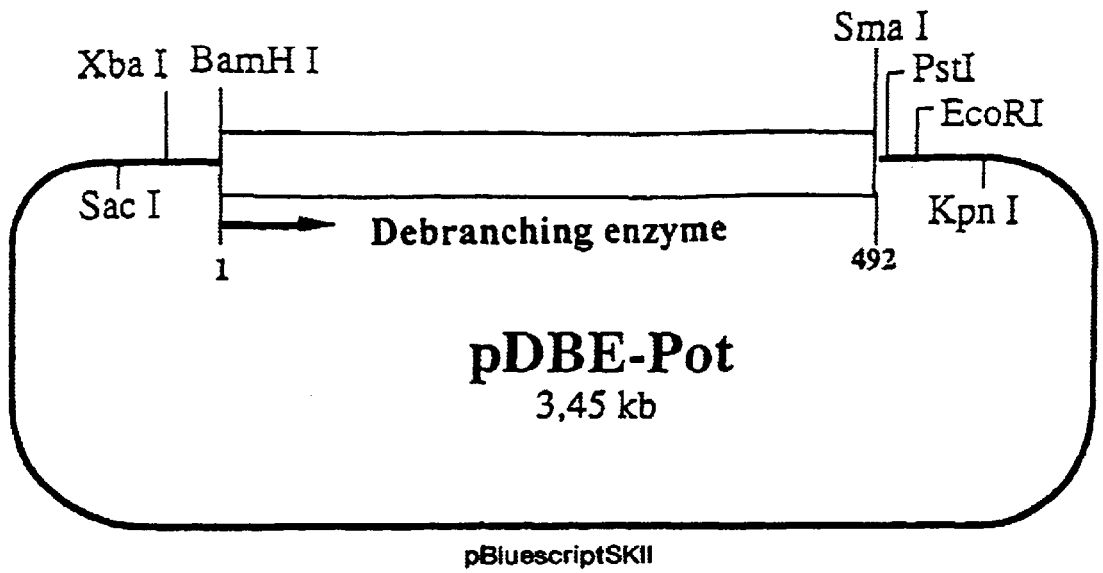

FIG. 4 shows plasmid pDBE-Pot

The thin line corresponds to the sequence of pBluescriptSKII(−). The thick line represents the partial cDNA sequence coding for part of the debranching enzyme from *Solanum tuberosum*. The arrow indicates the orientation of the coding region for the debranching enzyme. The cDNA insert is ligated between the BamHI and SmaI restriction sites of the polylinker of the plasmid. The DNA sequence of the cDNA insert is indicated in Seq ID No. 23.

Figure 5:
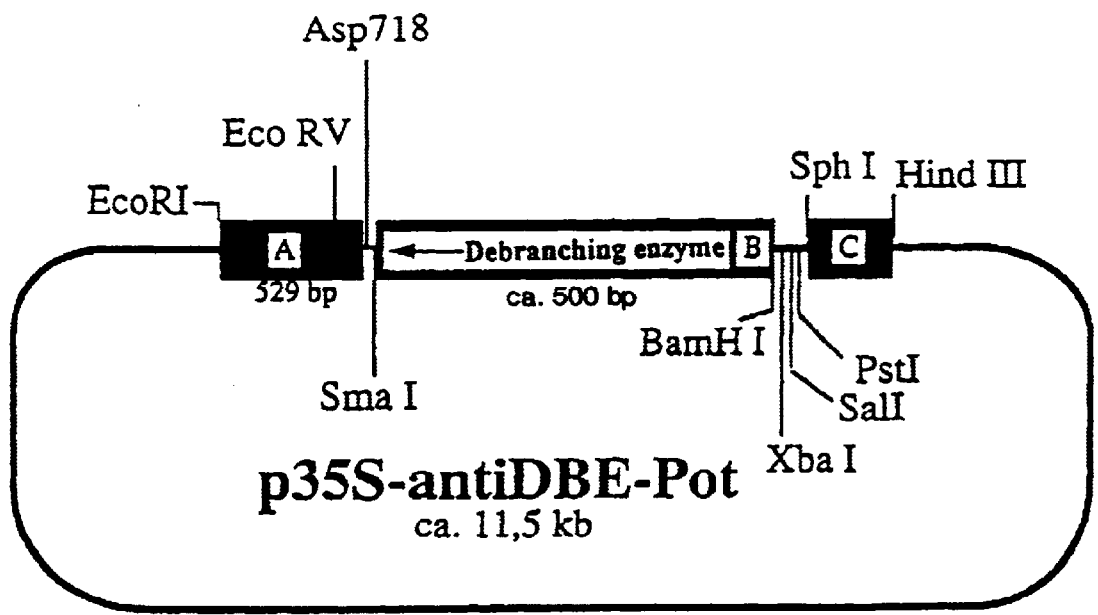

FIG. 5 shows plasmid p35S-antiDBE-Pot

A=fragment A: CaMV 35S promoter, nt 6909–7437 (Franck et al, Cell 21 (1980), 285–294)

B=fragment B: partial cDNA sequence from *Solanum tuberosum* coding for a part of the debranching enzyme;

SmaI/BamHI fragment from pDBE-Pot, about 500 bp; orientation towards the promoter: anti-sense C=fragment C: nt 11748–11939 of the T-DNA of the Ti plasmid pTiACH5 (Gielen et al., EMBO J. 3 (1984), 835–846)

Figure 6:
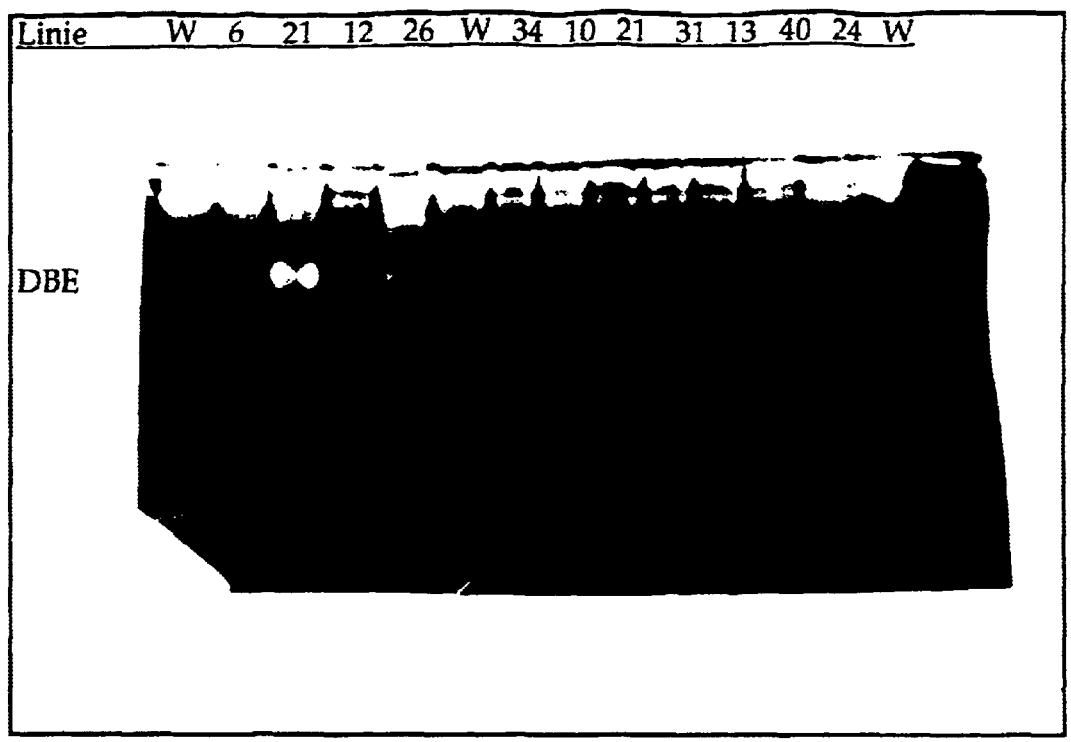

FIG. 6 shows an activity gel regarding the debranching enzyme from tuber extracts of potato plants (RE7 series) transformed with plasmid p35S-DBE-Spi and wild type plants.

DBE=debranching enzyme
W=wild type plant

The numbers indicate the plant lines examined.

Figure 7:
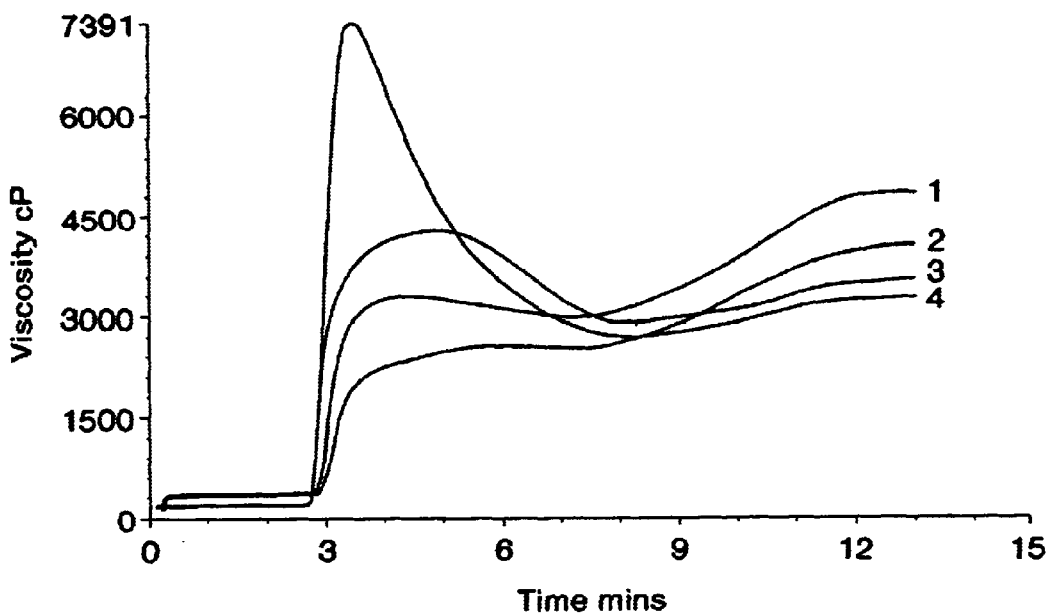

FIG. 7 shows curves of aqueous solutions of starch isolated from potato plants that were recorded with a Rapid Visco Analyser. Curves 1 to 3 indicate the viscosities of the solutions of starch obtained from the potato plants transformed with plasmid p35S-DBE-Spi. For a comparison, curve 4 represents the viscosity profile of the wild type starch.

Curve 1: plant line RE7-34,
Curve 2: plant line RE7-26,
Curve 3: plant line RE7-10,
Curve 4: wild type starch.

Figure 8:
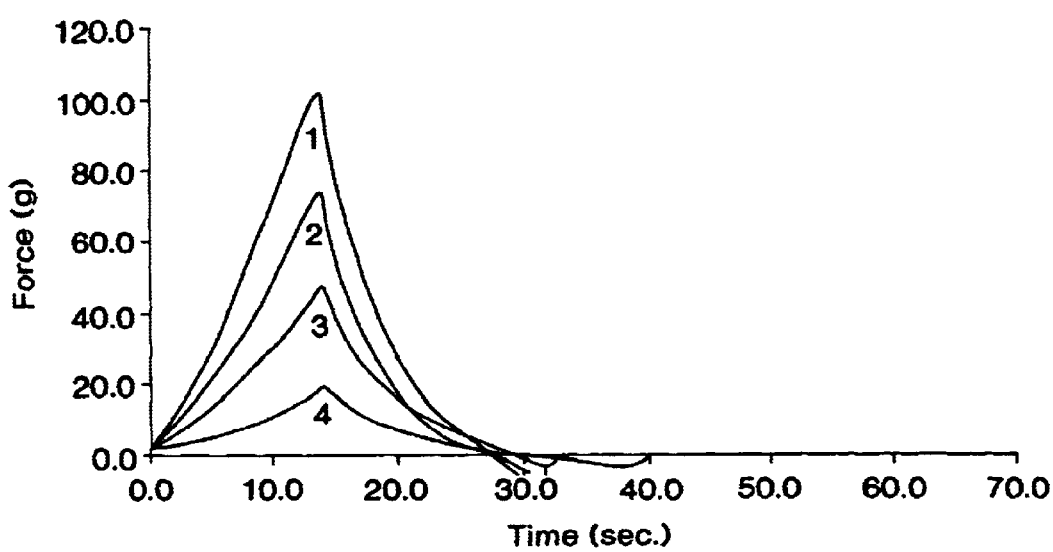

FIG. 8 shows the stability of the starch gels produced. The curves illustrate the force that is necessary to deform the gel. The force profiles 1 to 3 correspond to the starch that was obtained from the potato plants transformed with plasmid p35S-DBE-Spi. For a comparison, curve 4 indicates the force profile of the wild type starch;

Curve 1: plant line RE7-34,
Curve 2: plant line RE7-26,
Curve 3: plant line RE7-10,
Curve 4: wild type starch.

Figure 9:
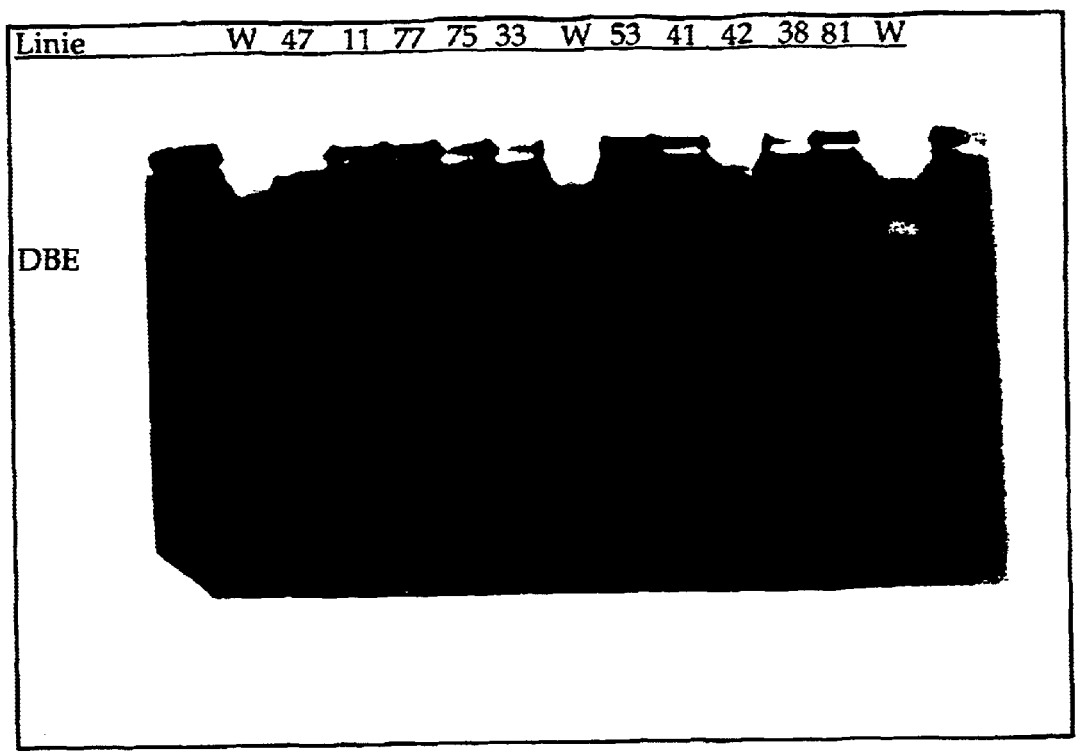

FIG. 9 shows an activity gel regarding the debranching enzyme from tuber extracts of potato plants (RE500 series) transformed with plasmid p35S-antiDBE-Pot and wild type plants.

DBE=debranching enzyme
W=wild type

The numbers indicate the plant lines examined.

Figure 10:
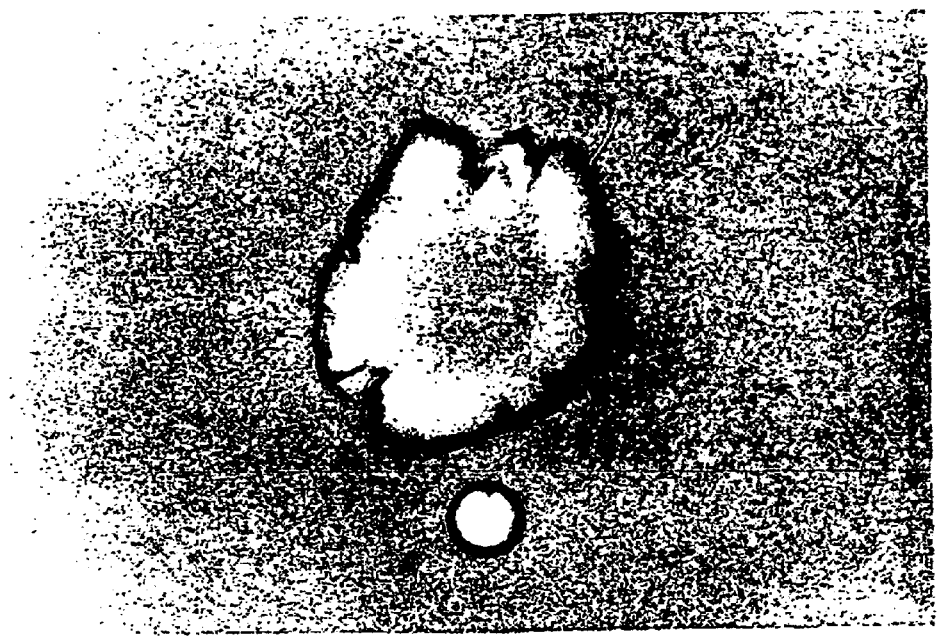

FIG. 10 Microscopic photograph of a starch granule from a potato plant transformed with plasmid p35S-antiDBE-Pot.

Figure 11:
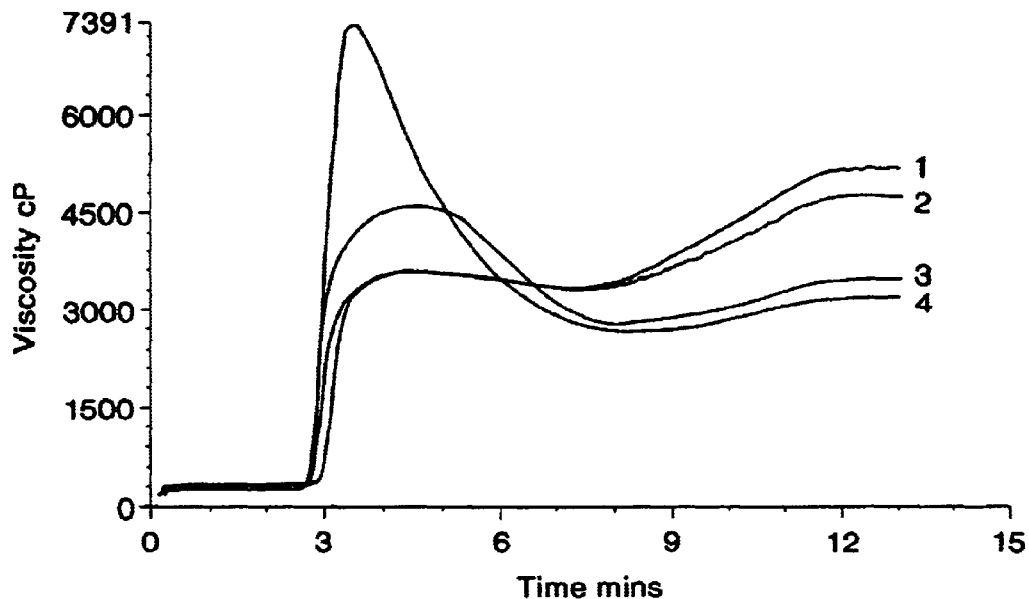

FIG. 11 shows curves of aqueous solutions of starch isolated from potato plants that were recorded with a Rapid Visco Analyser. Curves 1 to 3 indicate the viscosities of the solutions of starch obtained from the potato plants transformed with plasmid p35S-antiDBE-Pot. For a comparison, curve 4 represents the viscosity profile of the wild type starch.

Curve 1: plant line RE500-47,
Curve 2: plant line RE500-75,
Curve 3: plant line RE500-81,
Curve 4: wild type starch.

Figure 12:
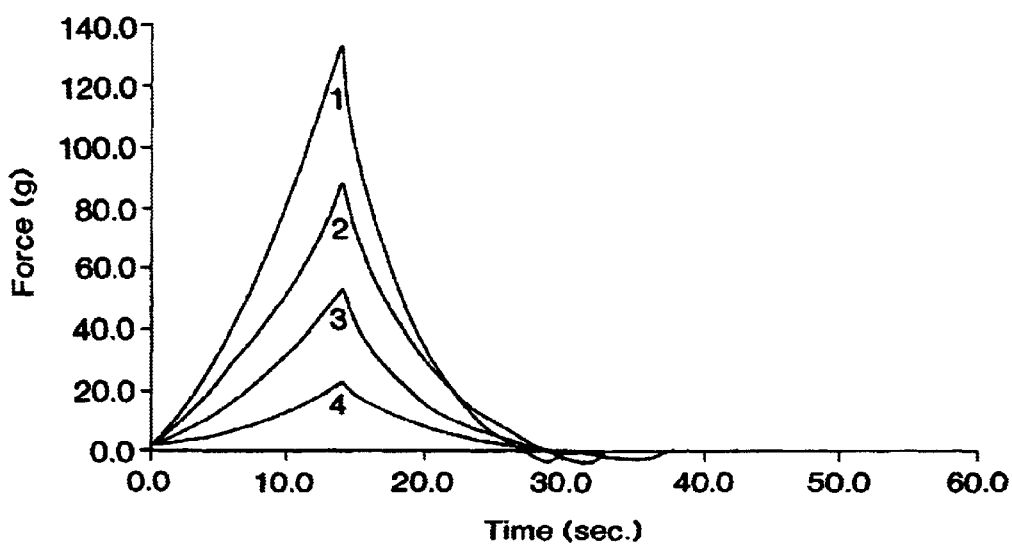

FIG. 12 shows the stability of the starch gels produced. The curves illustrate the force that is necessary to deform the gel. The force profiles 1 to 3 correspond to the starch that was obtained from the potato plants transformed with plasmid p35S-antiDBE-Pot. For a comparison, curve 4 indicates the force profile of the wild type starch:

Curve 1: plant line RE500-47,
Curve 2: plant line RE500-75,
Curve 3: plant line RE500-81,
Curve 4: wild type starch.

The examples serve to illustrate the invention.

In the following examples, the following techniques are used:

1. Cloning Techniques

For the cloning in *E. coli* the vectors pBluescriptSKII(−) (Stratagene) and pUC19 were used.

For the plant transformation the gene constructs were cloned into the binary vector pBinAR.

2. Bacterial Strains

For the Bluescript vectors, the pUC vectors and for the pBinAR constructs the *E. coli* strain DH5α (Bethesda Research Laboratories, Gaithersburgh, USA) were used. For in-vivo excision the *E. coli* strain XL1-Blue was used.

Transformation of the plasmids in the potato plants was carried out by using *Agrobacterium tumefaciens* strain C58C1 pGV2260 (Deblaere et al., Nucl. Acids Res. 13 (1985), 4777–4788).

3. Transformation of *Agrobacterium tumefaciens*

Transfer of the DNA was carried out by direct transformation according to the method by Höfgen and Willmitzer (Nucleic Acids Res. 16 (1988), 9877). The plasmid DNA of transformed Agrobacteria was isolated according to the method by Birnboim and Doly (Nucleic Acids Res. 7 (1979), 1513–1523) and subjected to gel electrophoretic analysis after suitable restriction.

4. Transformation of Potatoes

Ten small leaves of a potato sterile culture (*Solanum tuberosum* L.cv. Désirée) were wounded with a scalpel and placed in 10 ml MS medium (Murashige and Skook, Physiol. Plant. 15 (1962), 473) containing 2% sucrose which contained 50 μl of a selectively grown overnight culture of *Agrobacterium tumefaciens*. After gently shaking the mixture for 3–5 minutes it was further incubated in the dark for 2 days. For callus induction the leaves were placed on MS medium containing 1.6% glucose, 5 mg/l naphthyl acetic acid, 0.2 mg/l benzyl aminopurine, 250 mg/l claforan, 50 mg/l kanamycin, and 0.80% Bacto agar. After incubation at 25° C. and 3,000 lux for one week the leaves were placed for shoot induction on MS medium containing 1.6% glucose, 1.4 mg/l zeatin ribose, 20 mg/l naphthyl acetic acid, 20 mg/l giberellic acid, 250 mg/l claforan, 50 mg/l kanamycin and 0.80% Bacto agar.

5. Radioactive Labelling of DNA Fragments

The DNA fragments were radioactively labelled using a DNA Random Primer Labelling Kit of Boehringer (Germany) according to the manufacturer's information.

6. Northern Blot Analysis

RNA was isolated according to standard techniques from leave tissue of plants. 50 μg of RNA were separated in an agarose gel (1.5% agarose, 1×MEN buffer, 16.6% formaldehyde). The gel was shortly rinsed with water after gel run. The RNA was transferred with 20×SSC by capillary blot on a Hybond N nylon membrane (Amersham, UK). The RNA was then fixed on the membrane by UV cross-linking.

The membrane was prehybridized in NSEB buffer at 68° C. for 2 hrs and was then hybridized in NSEB buffer at 68° C. overnight in the presence of the radioactively labelled probe.

7. Plant Cultivation

Potato plants were cultivated in a greenhouse under the following conditions:

| | |
|---|---|
| Light period | 16 hrs at 25,000 lux and 22° C. |
| Dark period | 8 hrs at 15° C. |
| Humidity | 60% |

8. Detection of Debranching Enzymes in a Native Gel

For detection of debranching enzyme activity by non-denaturing gel electrophoresis tissue samples of potato tubers were broken up in 50 mM Tris-HCl (pH 7.6), 2 mM DTT, 2.5 mM EDTA, 10% glycerol and 0.4 mM PMSF. Electrophoresis was carried out in a MiniProtean II chamber (BioRad) under non-denaturing conditions according to Laemmli (Nature 227 (1970), 680–685). The monomer concentration of the gels with 1.5 mm thickness was 7.5% (w/v), and the gel contained 1% red pullulan (Megazyme, Australia). Equivalent amounts of protein extract were applied and separated for 2 hrs at 10 mA per gel.

The activity gels were then incubated in 100 mM sodium acetate (pH 6.0) and 0.1% β-mercaptoethanol at 37° C.

Debranching enzyme activity was detected by hydrolysis of the red pullulan (decoloring).

9. Starch Analysis

The starch produced by the transgenic potato plants was characterized by the following methods:

a) Determination of the Phosphate Content

In potato starch some glucose units may be phosphorylated at the carbon atoms at positions C3 and C6. In order to determine the phosphorylation degree at the C6 position of the glucose 100 mg starch were hydrolyzed in 1 ml 0.7 M HCl at 95° C. for 4 hours (Nielsen et al., Plant Physiol. 105 (1994), 111–117).

After neutralization with 0.7 M KOH, 50 µl of the hydrolysate were subjected to a photometric-enzymatic test to determine the glucose-6-phosphate content. The change of the absorption of the test mixture (100 mM imidazol/HCl; 10 mM $MgCl_2$; 0.4 mM NAD; 2 units glucose-6-phosphate dehydrogenase from *Leuconostoc mesenteroides*; 30° C.) was measured at 334 nm.

b) Determination of the Amylose/Amylopectin Ratio in Starch from Potato Plants

Starch was isolated from potato plants according to standard techniques and the amylose/amylopectin ratio was determined according to the method described by Hovenkamp-Hermelink et al. (Potato Res. 31 (1988), 241–246).

c) Determination of the Viscosity of the Aqueous Solution of the Starch

In order to determine the viscosity of the aqueous solutions of the starch synthesized by the transformed potato plants starch was isolated from tubers of transformed plants. 2 g starch each were dissolved in 25 ml $H_2O$ and used for analysis in a Rapid Visco Analyser (Newport Scientific Pty Ltd., Investment Support Group, Warriewood NSW 2102, Australia). The analyser was operated as indicated by the manufacturer. In order to determine the viscosity of the aqueous solution of the starch the starch suspension was first heated from 50° C. to 96° C. at a speed of 12° C. per minute.

Subsequently, the temperature was kept at 96° C. for 2.5 min. Afterwards, the solution was cooled from 96° C. to 50° C. at a speed of 16.4° C. per minute. During the entire test the viscosity was measured. Representative results of these measurements are illustrated as curves showing the viscosity in dependence of time.

d) Determination of the Stability of the Gel

For a further characterization of the starch its gel stability was measured using a TA-XT2 Texture Analyser (Stable Micro Systems, Unit 105, Blackdown Rural Industries, Haste Hill, Haslemere, Surrey Gu 27 3AY, England) following the manufacturer's recommendations.

The paste obtained from the Rapid Visco Analyser (see 9c) was stored at room temperature for 24 hours to form a gel. Then the gel stability was measured by allowing a plastic probe (d=10 mm) to penetrate the gel sample of 2 cm thickness at a speed of 0.5 mm/sec to a depth of up to 7 mm. The measurement yielded characteristic force profiles in dependence of time.

Abbreviations Used

| | |
|---|---|
| EDTA | ethylene diamine tetraacetic acid |
| IPTG | isopropyl β-D-thiogalacto-pyranoside |
| PAAG | polyacrylamide gel |
| PCR | Polymerase Chain Reaction |
| PMSF | phenylmethylsulfonyl fluoride |
| SDS | sodium dodecyl sulphate |

Materials and Solutions Used

| | | |
|---|---|---|
| Buffer A | 50 mM | sodium acetate (pH 6.0) |
| | 2.5 mM | 1,4-dithio-DL-threitol |
| | 1.5 mM | β-mercaptoethanol |
| | 0.4 mM | PMSF |
| | traces of sodium | bisulfite, sodium sulfite and ascorbic acid |
| Buffer B | 50 mM | MES |
| | pH 5.8 | with NaOH |
| Buffer C | 250 mM | phosphate buffer |
| | 250 mM | NaCl |
| | 1 mM | EDTA |
| | 7% | SDS |
| | 25% | PEG6000 |
| | 25% | formamide |
| | 250 mg/l | denatured herring sperm DNA |
| Buffer H | 2 × | SSC |
| | 10 × | Denhardt's solution |
| | 0.1% | SDS |
| | 5 mM | EDTA |
| | 50 mM | disodium phosphate |
| | 250 mg/l | herring sperm DNA |
| | 50 mg/ml | tRNA |
| 20 × SSC | 175.3 g | NaCl |
| | 88.2 g | sodium citrate |
| | ad | 1000 ml with $ddH_2O$ |
| | pH | 7.0 with 10 N NaOH |

EXAMPLE 1

Purification of a Debranching Enzyme from *Spinacia oleracea* and Determination of Peptide Sequences For purification of a debranching enzyme from spinach 500 g "deribbed" spinach leaves were homogenized in 1.5 l buffer B in a "Warring blender" for 1 min. The homogenate was strained through a sandwich of six layers of muslin cloth. If necessary, the pH was adjusted to a value of 5.8. The homogenate was subjected to centrifugation at 25,000×g for 30 min. Then proteins were precipitated from the supernatant by ammonium sulphate precipitation at 0° C. For this purpose, ammonium sulphate was continually added under stirring to the supernatant up to a concentration of 40% of the saturation concentration. Precipitation of proteins was continued under stirring for another 30 min. After separation of the precipitated proteins by centrifugation at 25,000×g for 30 min the resulting supernatant was mixed with ammonium sulphate up to a concentration of 50% of the saturation concentration. Precipitation was carried on for another 30 min. Then the mixture was centrifuged at 25,000×g for 30 min and the precipitated proteins were resuspended in about 80 ml buffer B. After centrifugation at 30,000×g for 15 min the supernatant was removed and applied to a affinity column which had been equilibrated with buffer B. The material of the affinity column was expoxy-activated sepharose 6B (Sigma) to which β-cyclodextrin (Cycloheptaamylose; Sigma) had been coupled as described by Ludwig et al. (Plant Physiol. 74 (1984), 856–861). The affinity column was washed with buffer B until the eluate did not exhibit any absorption at 280 nm. Elution of the debranching enzyme was carried out with 1 mg/ml β-cyclodextrin in buffer B. The fractions were assayed for debranching enzyme activity with the DNSS test (see Ludwig et al., loc. cit.) and were pooled. Removal of the cyclodextrin and concentration of the protein solution was carried out with Centricon 30 tubes (Amicon), with several washings with buffer B.

200 μg of the purified protein were cleaved with BrCN as described in Matsudaira ("A Practical Guide to Protein and Peptide Purification for Microsequencing", Academic Press, Inc., San Diego (1989), page 29). The resulting peptides were separated via SDS polyacrylamide gel electrophoresis. The gel used was a gradient gel in which the polyacrylamide concentration increased from 12% to 18% at a constant urea concentration of 6 M. The peptides were transferred from the SDS gel to a PVDF membrane by semi-dry-electroblotting. Peptide sequences of the isolated peptides were determined according to standard techniques. Two of the identified peptide sequences of the debranching enzyme of *Spinacia oleracea* are depicted in Seq ID No. 13 and Seq ID No. 14.

EXAMPLE 2
Isolation of a cDNA Coding for a Debranching Enzyme from Spinach

The peptide sequences of the debranching enzyme from spinach as obtained according to Example 1 were used to derive oligonucleotide sequences that represent regions of the DNA sequence of the gene coding for a debranching enzyme from spinach when considering the degeneracy of the genetic code. In accordance with the derived oligonucleotide sequences synthetic oligonucleotides were synthesized according to standard techniques. These oligonucleotides were used for amplification by PCR using mRNA from spinach leaves as template.

In order to allow for as efficient as possible hybridization of the oligonucleotides to the desired DNA fragment oligonucleotides with as great as possible length should be used. However, with increasing length the degree of degeneracy also increases, i.e., the number of oligonucleotides having different sequence combinations. Degrees of degeneracy of up to 6,000 are acceptable.

For the peptide sequence depicted in Seq ID No. 13 the sequence was derived for an oligonucleotide probe having a length of 20 bp. The oligonucleotide has a GC content of maximal 40% and minimal 30%. For the peptide sequence depicted in Seq ID No. 14 the sequence was derived for an oligonucleotide probe having a length of 20 bp. The oligonucleotide has a GC content of maximal 45% and minimal 35%.

The Sequence Template for the Synthesis of Oligonucleotides are:

```
Peptide A:  NH2-Gln Pro Ile Glu Thr Ile Asn Tyr Val-COOH  (Seq ID No. 13)

RNA:        5' CAR CCN AUH GAR ACN AUH AAY UAY GUN 3'

Oligo A:    3' TAC GTY GGW TAR CTY TGW TA 5'              (Seq ID No. 15)

Peptide B:  NH2-Asn Ile Asp Gly Val Glu Gly-COOH          (Seq ID No. 14))

mRNA:       5' AAY AUH GAY GGN GUN GAR GGN 3'

Oligo B:    5' AAY ATY GAT GGW GTI GAR GG 3'              (Seq ID No. 16)
```

The RNA was isolated from spinach leaves according to standard techniques. It was used for PCR using oligonucleotides A and B. 100 pmol each of the oligonucleotides per reaction mixture were used at an annealing temperature of 52° C. and a $MgCl_2$ concentration of 1.5 mM. 30 cycles were carried out. PCR yielded a DNA fragment of about 500 bp.

This DNA fragment was ligated into vector pUC19 which was cleaved with SmaI. The resulting plasmid was called pAR1. A part of the sequence of the DNA insert was determined using the method of Sanger et al. (Proc. Natl. Acad. Sci. USA 74 (1977), 5463–5467). The determined sequence corresponds to nucleotides 1920 to 2216 of the DNA sequence depicted in Seq ID No. 17 except for the mismatches introduced by the degenerate oligonucleotides. The amino acid sequence derived from said sequence exhibits an identity of 42.2% to the pulA gene from *Klebsiella aerogenes* coding for a pullulanase over a range of 90 amino acids.

For isolation of cDNA molecules coding for the debranching enzyme of spinach a cDNA library was constructed in the vector Lambda ZAP II (Stratagene) as described by Sonnewald et al. (Planta 189 (1993), 174–181) and was packaged in phage heads. Subsequently, *E. coli* cells of the XL1-Blue strain were infected with the phages containing the cDNA fragments and plated on a medium in Petri dishes in a density of about 30,000 per 75 $cm^2$. After about 8 hrs of incubation nitrocellulose membranes were placed on the lysed bacterial layer and were removed after one minute. The filters were incubated for 2 min in 0.2 M NaOH; 1.5 M NaCl, then for 2 min in 0.4 M Tris/HCl (pH 7.5) and finally for 2 min in 2×SSC. The filters were dried, UV cross-linked and incubated at 42° C. for 3 hrs in buffer C before the radioactively labelled probe was added. As probe the cDNA insert of plasmid pAR1 was used. Hybridization was carried out at 42° C. for 12 to 16 hrs. The filters were then washed at 45° C. once for 15 min in 1×SSC/0.3% SDS and three times for 15 min in 0.1×SSC/0.3% SDS and then subjected to autoradiography.

Positive phage clones were individualized and further purified by standard techniques. The in-vivo excision method was used to obtain from positive phage clones *E. coli* clones containing a double-stranded pBluescript plasmid having the corresponding cDNA insert. After examination of the size and restriction pattern of the inserts the DNA sequence of suitable clones was determined. Several clones were identified that contain inserts coding for the debranching enzyme from spinach, particularly a clone exhibiting a cDNA insert including nucleotides 1804 to 3067 of the DNA sequence depicted in Seq ID No. 17. However, no complete clones were obtained.

In order to isolate cDNA molecules comprising the entire coding region for the debranching enzyme, a specific cDNA library with mRNA from spinach leaves was established. For this purpose total RNA from spinach leaves was isolated according to standard techniques. In order to obtain poly (A$^+$) mRNA the total RNA was applied to a poly(dT) column from which poly(A$^+$) mRNA was eluted.

Starting from the poly(A$^+$) mRNA cDNA was prepared according to the method of Gubler and Hoffmann (Gene 25 (1983), 263–269) using an XhoI oligo d(t)$_{18}$ primer. The cDNA was cleaved with XhoI after EcoRI linker addition and ligated in an oriented manner into a Lambda Uni-ZAP XR vector (Stratagene) which had been cleaved with EcoRI and XhoI. About 2,000,000 plaques of a cDNA library so constructed were screened for cDNA sequences coding for the debranching enzyme. For this purpose *E. coli* cells of the XL1-Blue strain were infected with the phages containing the cDNA fragments and plated on a medium in Petri dishes in a density of about 30,000 per 75 cm$^2$. After about 8 hrs of incubation nitrocellulose membranes were placed on the lysed bacterial layer and were removed after one minute. The filters were incubated for 2 min in 0.2 M NaOH; 1.5 M NaCl, then for 2 min in 0.4 M Tris/HCl (pH 7.5) and subsequently for 2 min in 2×SSC. The filters were dried, UV cross-linked and incubated at 42° C. for 3 hrs in buffer C before the radioactively labelled probe was added. As probe either the cDNA inserts described above that contained only parts of the coding region for the debranching enzyme, or the insert of plasmid pAR1 was used. After hybridization at 42° C. for 12 hrs the filters were washed at 45° C. once for 15 min in 1×SSC/0.3% SDS and three times for 15 min in 0.1×SSC/0.3% SDS and then subjected to autoradiography.

Positive phage clones were individualized and further purified by standard techniques. The in-vivo excision method was used to obtain from positive phage clones *E. coli* clones containing a double-stranded pBluescript plasmid having the corresponding cDNA insert. After examination of the size and restriction pattern of the inserts the plasmid DNA of suitable clones was isolated and the DNA sequence of the cDNA insert was determined.

EXAMPLE 3
Sequence Analysis of the cDNA Insert of Plasmid pDBE-Spi

From an *E. coli* clone obtained according to Example 2 plasmid pDBE-Spi (FIG. 1) was isolated and its cDNA insert determined according to standard techniques using the didesoxy method (Sanger et al., Proc. Natl. Acad. Sci. USA 74 (1977), 5463–5467). The insert has a length of 3437 bp. The nucleotide sequence and the derived amino acid sequence is indicated in Seq ID No. 17.

EXAMPLE 4
Construction of Plasmid p35S-DBE-Spi, Transformation of Potato Plants as well as Characterization of the Synthesized Starch From plasmid pDBE-Spi a DNA fragment of about 3450 bp length was obtained by EcoRI/XhoI digestion which exhibits the sequence indicated in Seq ID No. 17 and contains the coding region for the spinach debranching enzyme. This DNA fragment was cloned into the vector pBinAR (Höfgen and Willmitzer, Plant Sci. 66 (1990), 221–230) which had been cleaved with SmaI. The vector pBinAR is a derivative of the binary vector pBin19 (Bevan, Nucl. Acids Res. 12 (1984), 8711–8721). Construction of plasmid pBinAR is described in Example 12. The resulting plasmid was called p35S-DBE-Spi and is depicted in FIG. 2.

Insertion of the cDNA fragment results in an expression cassette which consists of fragments A, B and C as follows (FIG. 2):

Fragment A (529 bp) contains the 35S promoter of cauliflower mosaic virus (CaMV). The fragment includes nucleotides 6909 to 7437 of CaMV (Franck et al., Cell 21 (1980), 285–294).

Fragment B comprises the protein-encoding region as well as the flanking regions of the cDNA coding for spinach debranching enzyme. It was isolated as EcoRI/XhoI fragment from pDBE-Spi as described above and fused to the promoter in pBinAR in sense orientation.

Fragment C (192 bp) contains the polyadenylation signal of the gene 3 of the T-DNA of the Ti plasmid pTiACH5 (Gielen et al., EMBO J. 3 (1984), 835–846).

The size of plasmid p35S-DBE-Spi is about 14.2 kb.

Vector p35S-DBE-Spi was transferred to potato plant cells via *Agrobacterium tumefaciens*-mediated transformation. Intact plants were regenerated from the transformed cells. Analysis of RNA for the presence of an mRNA coding for the spinach debranching enzyme can be used to verify if the genetic modification was successfully established. For this purpose, usually a northern blot analysis is made. Total RNA is isolated from plant tissue as described by Logemann et al. (Anal. Biochem. 163 (1987), 16–20), separated via gel electrophoresis, transferred to a nylon membrane and hybridized to a suitable probe.

As a result of the transformation transgenic potato plants showed increased debranching enzyme activity (cf. FIG. 6).

The starch produced by these plants is subsequently analyzed and characterized. The starch produced by the transgenic plants differs from the starch synthesized by wild type plants as regards its viscosity and gel stability.

The viscosity was determined using a Rapid Visco Analyser according to the method described above. The results are shown in FIG. 7. FIG. 7 shows in curve 4 a typical RVA-curve for starch isolated from wild type plants of the potato variety Désirée. Curves 1 to 3 of the transformed plant lines have a considerably less marked to no viscosity maximum at all after heating to 96° C. as well as a higher increase in viscosity after cooling to 50° C. The maximum viscosity of the starch from the transgenic p35S-DBE-Spi plants has a substantially reduced value as compared to starch from wild type plants. The final viscosity of the modified starch after subsequent cooling is considerably higher than the values for starch synthesized in wild type plants.

FIG. 8 illustrates the gel stability of gels prepared from starch of transgenic plant lines as compared to gels from wild type starch. The gel stability of the modified starch differs considerably. The force that is necessary to deform gels of modified starch is greater than the force that is necessary to deform a corresponding gel prepared from wild type starch.

The phosphate content of the starch produced in the transgenic plants approximately corresponds to the value for the starch produced in wild type plants (see Table 1). The measuring inaccuracy is about ±5%.

The amylose content can be calculated according to Hovenkamp-Hermelink et al. (Potato Res. 31 (1988), 241–246).

The amylose content is slightly increased by 5 to 40% (see Table 1).

TABLE 1

| Plants | nmol glucose-6-phosphate/mg starch | % amylose |
|---|---|---|
| Wild type | 9.00 | 20.4 |
| RE7-10 | 10.80 | 21.7 |
| RE7-26 | 8.23 | 21.8 |
| RE7-34 | 8.49 | 24.3 |

The plant line RE7-34 shows the most significant deviations from the wild type plant.

EXAMPLE 5
Identification and Isolation of Genomic DNA Sequences Coding for a Debranching Enzyme of Solanum tuberosum Identification and isolation of genomic DNA sequences coding for a debranching enzyme of Solanum tuberosum was carried out such that first proteins having the enzymatic activity of a debranching enzyme were isolated from potatoes, peptide sequences of these proteins were determined and from these peptide sequences degenerate oligonucleotide sequences were derived that were used for screening genomic libraries. This process is described in the following in detail.

(a) Identification of a New Debranching Enzyme in Solanum tuberosum

Identification of a new debranching enzyme in Solanum tuberosum was carried out according to known methods as described below:

Protein extracts were obtained from tuber tissue of plants of the species Solanum tuberosum. For this purpose, 820 g tuber tissue were homogenized in 1500 ml buffer A. Of this homogenate 50 ml were separated in a PAAG (see lane 0 in FIG. 3). The gel contained 7.5% acrylamide (pH 7.9) which was linked with methylene bisacrylamide up to a degree of 1:75, as well as 1% amylopectin. The buffer system for electrophoresis contained tris/glycin (pH 7.9). After gel run the gel was equilibrated in 50 mM tris/citrate (pH 7.0); 2 mM ascorbic acid at 22° C. for 4 hrs. The gel was stained with Lugol's solution for 15 min. The result of the staining is shown in FIG. 3, lane 0. In addition to the reddish band that is the result of the activity of a branch-introducing enzyme (branching enzyme of disproportionating enzyme) a band with a strong blue stain can be observed. The blue staining is the result of the enzymatic digestion of α-1,6-glycosidic branches of the amylopectin which accounts for its reddish or purple color.

(b) Purification of a Debranching Enzyme from Solanum tuberosum and Detection of Peptide Sequences Purification of a debranching enzyme from Solanum tuberosum and detection of peptide sequences was carried out according to known methods as follows:

For purification of a debranching enzyme from potato 500 g tuber tissue were homogenized in 1.5 l buffer B in a "Warring blender" for 1 min. The homogenate was strained through a sandwich of six layers of muslin cloth. If necessary, the pH was adjusted to a value of 5.8. The homogenate was subjected to centrifugation at 25,000×g for 30 min. Then proteins were precipitated from the supernatant by ammonium sulphate precipitation at 0° C. For this purpose, ammonium sulphate was continually added under stirring to the supernatant up to a concentration of 40% of the saturation concentration. When precipitation of proteins began, the mixture was stirred for another 30 min. After separation of the precipitated proteins by centrifugation at 25,000×g for 30 min the resulting supernatant was mixed with ammonium sulphate up to a concentration of 50% of the saturation concentration. Precipitation was carried on for another 30 min. Then the mixture was centrifuged at 25,000×g for 30 min and the precipitated proteins were resuspended in about 80 ml buffer B. After centrifugation at 30,000×g for 15 min the supernatant was removed and applied to an affinity column which had been equilibrated with buffer B. The material of the affinity column was expoxy-activated sepharose 6B (Sigma) to which β-cyclodextrin (Cycloheptaamylose; Sigma) had been coupled as described by Ludwig et al. (Plant Physiol. 74 (1984), 856–861). The affinity column was washed with buffer B until the eluate did not exhibit any absorption at 280 nm. A protein fraction having low affinity to the stationary phase was eluted using a β-cyclodextrin solution (1 mg/ml in buffer A) and was then discarded. At a β-cyclodextrin concentration of 10 mg/ml in buffer A the potato debranching enzyme was eluted (cf. FIG. 3).

The fraction of the eluate which was rich in debranching enzyme was subjected to electrophoresis in a denaturing PAAG according to the method of Laemmli (Nature 227 (1970), 680–685). The denatured protein was cut out from the gel and isolated. Peptide sequences were determined according to standard techniques. Peptide sequences of the debranching enzyme from Solanum tuberosum are shown in Seq ID No. 1 to Seq ID No. 12.

(c) Identification and Isolation of Genomic DNA Sequences Coding for a Debranching Enzyme of Solanum tuberosum by Using Genetic Engineering The peptide sequences as obtained according to section (b) were used to derive oligonucleotide sequences which represent regions of the gene coding for potato debranching enzyme when considering the degeneracy of the genetic code. Synthetic oligonucleotides were synthesized according to standard techniques in accordance with the derived oligonucleotide sequences. These synthetic oligonucleotides were used to screen genomic libraries.

First a genomic DNA library was constructed according to Liu et al. (Plant Mol. Biol. 17 (1991), 1139–1154). Subsequently, E. coli cells of the strain P2392 were infected with the phages containing the genomic DNA fragments and plated on a medium in Petri dishes in a density of about 30,000 per 75 cm². The Petri dishes were incubated at 37° C. until the phage plaques had reached a suitable size (about 6–8 hrs). Then the Petri dishes were stored at 4° C. for several hours. Nitrocellulose membranes were placed on the lysed bacterial layer and were removed after one minute. The filters were incubated for 2 min in 0.2 M NaOH; 1.5 M NaCl, then for 2 min in 0.4 M Tris/HCl (pH 7.5) and finally for 2 min in 2×SSC. The filters were dried, UV cross-linked and incubated for 3 hrs in buffer H before the radioactively end-labelled oligonucleotides were added. After hybridization for 12 hrs the filters were washed two times for 15 min in 0.2×SSC/0.1% SDS and then subjected to autoradiography.

The temperature for hybridization and washing of the filters can be calculated as follows:

$$T+15=16.6\times[Na^+]+0.41\times[\% \ GC_{oligonucleotide}]+81.5-675/\text{length}_{oligonucleotide}$$

The peptide sequences of the potato debranching enzyme depicted in Seq ID No. 1 or Seq ID No. 5 can be used to derive suitable oligonucleotide sequences. In order to achieve as high as possible hybridization temperature allowing sufficient specificity for hybrid formation, as long as possible oligonucleotides should be used. With increasing length, however, the degree of degeneracy also increases, i.e., the number of oligonucleotides having different sequence combinations. Degrees of degeneracy of up to 6,000 are acceptable. If several peptide sequences are known for a protein, corresponding oligonucleotides can be derived, combined and used as an oligonucleotide mixture for hybridization, thus increasing efficiency of hybridization.

For a part of the peptide sequence indicated in Seq ID No. 1 the sequence for an oligonucleotide probe of 20 bp length was derived. The oligonucleotide had a degree of degeneracy of 256 at a GC content of maximal 65% and minimal 40%, resulting in a maximum hybridization temperature of about 56° C. For a part of the peptide sequence indicated in Seq ID No. 5 the sequence for an oligonucleotide probe of 20 bp length was derived. The oligonucleotide had a degree of degeneracy of 384 at a GC content of maximal 55% and minimal 50%, resulting in a maximum hybridization temperature of about 60° C. Both oligonucleotides were used for hybridization as a mixture at a temperature of 54° C. The filters were washed at a temperature of 45° C.

The Sequence Template for the Synthesis of the Probes was as Follows:

For this purpose, a nitrocellulose membrane was placed on a solid medium in a Petri dish. Onto this membrane cells of *E. coli* colonies were transferred. The petri dish was incubated at 37° C. overnight and the *E. coli* cells on the membrane grew to colonies. The membrane was removed from the medium and incubated for 5 min in 10% SDS, 5 min in 0.5 M NaOH; 1.5 M NaCl, then for 5 min in 0.5 M Tris/HCl (pH 7.5) and subsequently for 5 min in 2×SSC. The filters were dried, UV cross-linked and incubated for 3 hrs in buffer H before radioactively end-labelled oligonucleotides were added. For hybridization the radioactively labelled probes 1 (Seq ID No. 19) and 2 (Seq ID No. 20) were used. After hybridization at 54° C. for 12 hrs the filters were washed at 45° C. two times for 15 min in 0.2×SSC/ 0.1% SDS and subjected to autoradiography. Bacteria of colonies hybridizing to the probe used were cultivated and plasmid DNA was isolated from the cells. In this manner various plasmids containing inserts that hybridized to the oligonucleotides used were isolated. Subsequently, part of the DNA sequence of the inserts of the isolated plasmids were determined according to the method of Sanger et al. (Proc. Natl. Acad. Sci. USA 74 (1977), 5463–5467).

EXAMPLE 6

Isolation of cDNA Sequences Coding for a Debranching Enzyme from *Solanum tuberosum* Using Polymerase Chain Reaction The partial genomic DNA sequences obtained in Example 5 were compared with the spinach cDNA sequence coding

```
Peptide 1:  NH2-Asp Ser Asp Asp Val Lys Pro Glu Gly-COOH  (Amino acids 8-16 in Seq ID No. 1)

mRNA:       5' GAY GAY GUN AAR CCN GAR GG 3'

Probe 1:    3' CTR CTR CAN TTY GGN CTY CC 5'              (Seq ID No. 19)

Peptide 5:  NH2-Ile Gln Val Gly Met Ala Ala-COOH          (Amino acids 3 bis 9 in Seq ID No.
                                                           5)

mRNA:       5' AUH CAR GUN GUN AUG GCN CC 3'

Probe 2:    3' TAD GTY CAI CCI TAC CGI CC 5'              (Seq ID No. 20)
```

In three screening cycles phage clones containing a DNA insert hybridizing to the probes used were individualized. In this manner about 40 plaques were identified when screening about 500,000 phage plaques.

These positive phage clones were used for hybridization to the cDNA sequence (Seq ID No. 17) isolated from spinach which codes for a debranching enzyme. In this way 3 phage clones could be isolated which also hybridize with for the debranching enzyme. It was found that two of the identified inserts comprised DNA sequences that are homologous to two DNA sequences that are located in the spinach cDNA in a distance of about 500 bp from each other. Starting from these sequences two oligonucleotides were synthesized for PCR reaction. These two oligonucleotides had the following nucleotide sequences:

```
Oligonucleotide C
5' AAGGTACCGG ATCCTCTGCT GATGGCAAGT GGACATTATT AGT 3'    (Seq ID No. 21)

Oligonucleotide D
5' TTAAGCCCGG GCGATACGAC AAGGACCATT TGCATTACCA G 3'      (Seq ID No. 22)
``` the cDNA sequence from spinach. From one of the identified lambda phage clones, λDEpot, DNA was obtained according to standard techniques, the DNA insert was isolated and cleaved with the restriction endonuclease Sau3A. The resulting subfragments were ligated into a pBluescript vector which had been cleaved with BamHI. *E. coli* cells were transformed with the resulting plasmids. Transformed bacteria were plated on medium in Petri dishes. In order to determine which bacteria contain DNA inserts coding for debranching enzyme a colony hybridization was performed.

Oligonucleotide C serves to introduce a BamHI restriction site at one end of the amplified DNA fragment. This oligonucleotide is partially homologous to the spinach cDNA in the range of nucleotides 1082 to 1110 of the DNA sequence depicted in Seq ID No. 17. Oligonucleotide D serves to introduce a SmaI restriction site at the other end of the fragment to be amplified. This oligonucleotide is homologous to the spinach cDNA in the range of nucleotides 1545 to 1571 of the DNA sequence depicted in Seq ID No. 17.

These oligonucleotides were used for the amplification of a DNA fragment from a potato tuber cDNA library.

For this purpose, a cDNA library was established by preparing total RNA from the tuber tissue of potato according to Logemann et al. (Anal. Biochem. 163 (1987), 16–20). Polyadenylated mRNA was prepared from the total RNA according to standard techniques and was used for the synthesis of cDNA according to the method described by Gubler and Hoffmann (Gene 25 (1983), 263). The cDNA was ligated with commercially available EcoRI/NotI adapters, ligated into the EcoRI restriction site of the DNA of phage Lambda ZAP II (Stratagene) and packaged in phage heads. From a cDNA library so constructed a DNA fragment of about 500 bp length was amplified by PCR using oligonucleotides C and D. This DNA fragment was cleaved with the restriction endonucleases BamHI and SmaI and ligated into a pBluescript vector which had been cleaved with BamHI and SmaI. The resulting plasmid was called pDBE-Pot (FIG. 4).

The isolated 500 bp fragment serves to isolate cDNA fragments comprising the entire coding region for potato debranching enzyme from a cDNA library in Lambda ZAP II constructed as described above by using conventional molecular genetic techniques.

EXAMPLE 7
Sequence Analysis of the cDNA Insert of Plasmid pDBE-Pot

From an *E. coli* clone obtained according to Example 6 plasmid pDBE-Pot (FIG. 4) was isolated and its cDNA insert determined according to the standard didesoxy method (Sanger et al., Proc. Natl. Acad. Sci. USA 74 (1977), 5463–5467).

The insert has a length of 492 bp. The nucleotide sequence is indicated in Seq ID No. 23.

Analysis of the DNA sequence showed that the peptide sequences indicated in Seq ID No. 1 and in Seq ID No 2 are coded for by the DNA sequence indicated in Seq ID No. 23, with deviations at two positions each. Seq ID No. 1 corresponds to amino acids 6 to 26 of the amino acid sequence indicated in Seq ID No. 23 and Seq ID No. 2 corresponds to amino acids 80 to 99 of the amino acid sequence indicated in Seq ID No. 23. The deviations can be accounted for by the fact that the protein was isolated from potatoes of the variety Désirée, the cDNA library used, however, was constructed from potatoes of the variety Berolina.

EXAMPLE 8
Construction of Plasmid p35S-antiDBE-Pot, Transformation of Potato Plants as Well as Characterization of the Starch Synthesized A DNA fragment of about 500 bp length was isolated from plasmid pDBE-Pot by digestion with BamHI/SmaI, which fragment has the sequence indicated in Seq ID No. 23 and contains part of the coding region for potato debranching enzyme. This DNA fragment was cloned into vector pBinAR (Höfgen and Willmitzer, Plant Sci. 66 (1990), 221–230) which had been cleaved with BamHI/SmaI. Vector pBinAR is a derivative of binary vector Bin19 (Bevan, Nucleic Acids Res. 12 (1984), 8711–8721).

pBinAR was constructed as follows:

A fragment of 529 bp length comprising nucleotides 6909–7437 of the 35S promoter of the cauliflower mosaic virus (Franck et al., Cell 21 (1980), 285–294) was isolated as EcoRI/KpnI fragment from plasmid pDH51 (Pietrzak et al., Nucl. Acids Res. 14, 5857–5868) and ligated between the EcoRI and KpnI restriction sites of the polylinker of pBin19, resulting in plasmid pBin19-A.

A fragment of 192 bp length was isolated from plasmid pAGV40 (Herrera-Estrella et al., Nature 303, 209–213) using the restriction endonucleases PvuII and HindIII, which fragment comprises the polyadenylation signal of gene 3 of the T-DNA of Ti plasmid pTiACH5 (Gielen et al., EMBO J. 3, 835–846) (nucleotides 11749–11939). After addition of SphI linkers to the PvuI restriction site the fragment was ligated into pBin19-A which had been cleaved with SphI and HindIII, resulting in pBinAR.

The resulting plasmid was called p35S-antiDBE-Pot and is depicted in FIG. 5.

Insertion of the cDNA fragment results in an expression cassette that is composed of fragments A, B and C as follows (FIG. 5):

Fragment A (529 bp) contains the 35S promoter of the cauliflower mosaic virus (CaMV). The fragment comprises nucleotides 6909 to 7437 of CaMV (Franck et al., Cell 21 (1980), 285–294).

Fragment B comprises part of the protein-encoding region of the cDNA coding for potato debranching enzyme. This part was isolated from pDBE-Pot as BamHI/SmaI fragment as described above and fused to the promoter in pBinAR in anti-sense orientation.

Fragment C (192 bp) contains the polyadenylation signal of gene 3 of the T-DNA of Ti plasmid pTiACH5 (Gielen et al., EMBO J. 3 (1984), 835–846).

The size of the plasmid p35S-antiDBE-Pot is about 11.5 kb. Vector p35S-antiDBE-Pot was transferred to potato plant cells via *Agrobacterium tumefaciens*-mediated transformation. Intact plants were regenerated from the transferred cells. An analysis of the total RNA for the absence of endogenous mRNA coding for the debranching enzyme can be used to verify if the plants have been successfully genetically modified.

As a result of transformation, transgenic potato plants exhibited a reduced debranching enzyme activity (cf. FIG. 9).

In contrast to the starch granules from wild type plants which have a regular round shape the starch granules produced by transgenic plants have a rough, chapped or even frayed surface (see FIG. 10).

The starch synthesized by transgenic plants furthermore differs from that synthesized by wild type plants in its viscosity during gelation ("pasting"), in its gel stability and phosphate content.

Viscosity was determined with a Rapid Visco Analyser according to the method described above. The results are shown in FIG. 11. FIG. 11 in curve 4 shows a typical RVA curve for starch isolated from wild type plants of the potato variety Désirée. Curves 1 to 3 of the transformed plant lines have a considerably less marked viscosity maximum after heating to 96° C. as well as a higher increase in viscosity after cooling to 50° C., i.e., a higher final viscosity.

FIG. 12 shows the gel stability of gels prepared from starch of the inhibited plant lines as compared to gel from wild type starch. The gel stability of the modified starch is substantially different. The force that is necessary to deform the gel is substantially greater than the force that is necessary to deform a corresponding gel prepared from wild type starch.

The phosphate content of the starch synthesized by transgenic plants is—also dependent on the degree of antisense-inhibition—above the value for starch synthesized by wild type plants (see Table 2). The measuring inaccuracy is about ±5%.

The amylose content is calculated according to Hovenkamp-Hermelink et al. (Potato Res. 31 (1988), 241–246). Depending on the transgenic plant line the amylose content is approximately the same or slightly increased vis-á-vis the amylose content of wild type starch (see Table 2).

TABLE 2

| Plants | nmol glucose-6-phosphate/mg starch | % amylose |
| --- | --- | --- |
| Wild type | 9.00 | 20.4 |
| RE500-47 | 14.66 | 21.7 |
| RE500-81 | 11.19 | 19.7 |
| RE500-75 | 10.42 | 22.5 |

What is claimed is:

1. An isolated plant protein having the enzymatic activity of a debranching enzyme, or an enzymatically active fragment thereof, wherein the protein is not a potato protein or a spinach protein, and wherein the protein is encoded by a DNA molecule that hybridizes to the coding region of SEQ ID NO: 17 or the coding region of SEQ ID NO: 23 under the following conditions; hybridization at 42° C. followed by a wash at 45° C. in 0.1×SSC/0.3% SDS solution or 0.2×SSC/0.1% SDS solution.

2. The plant protein according to claim 1, wherein the protein comprises a peptide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13 and SEQ ID NO: 14.

3. The plant protein according to claim 1, wherein the DNA molecule is from a starch-synthesizing or starch-storing plant.

4. The plant protein according to claim 3, wherein the DNA molecule is from a plant selected from the group consisting of: barley, rye, oat, wheat, maize, rice, pea and cassava.

5. The plant protein according to claim 1, wherein the protein is obtained from a host cell comprising the DNA molecule.

6. An isolated plant protein having the enzymatic activity of a debranching enzyme, or an enzymatically active fragment thereof, wherein the protein is not a potato protein or a spinach protein, wherein the protein is obtained from a plant cell comprising an isolated DNA molecule selected from the group consisting of:

(a) a DNA molecule coding for a protein comprising the amino acid sequence of SEQ ID NO: 18;

(b) a DNA molecule comprising the coding region of SEQ ID NO: 17;

(c) a DNA molecule coding for a protein comprising the amino acid sequence of SEQ ID NO: 24;

(d) a DNA molecule comprising the coding region of SEQ ID NO: 23;

(e) a DNA molecule, wherein the nucleotide sequence of the DNA molecule deviates from the nucleotide sequence of a DNA molecule according to (a), (b), (c) or (d) due to the degeneracy of the genetic code;

(f) a DNA molecule that hybridizes to a DNA molecule according to (a), (b), (c), (d) or (e) under the following conditions: hybridization at 42° C. followed by a wash at 45° C. in 0.1×SSC/0.3% SDS solution or 0.2×SSC/0.1% SDS solution; and (g) a DNA molecule according to any one of the DNA molecules according to (a)–(f), wherein the plant protein comprises at least one of the peptide sequences of SEQ ID NOs: 1–14.

7. An isolated plant protein encoded by a DNA molecule, wherein the DNA molecule is selected from the group consisting of:

(a) a DNA molecule coding for a protein comprising the amino acid sequence of SEQ ID NO: 18;

(b) a DNA molecule comprising the coding region of SEQ ID NO: 17;

(c) a DNA molecule coding for a protein comprising the amino acid sequence of SEQ ID NO: 24; and (d) a DNA molecule comprising the coding region of SEQ ID NO: 23.

* * * * *

SEQUENCE LISTING

<160> NUMBER OF SEQ ID NOS: 24

<210> SEQ ID NO 1
<211> LENGTH: 21
<212> TYPE: PRT
<213> ORGANISM: Solanum tuberosum

<400> SEQUENCE: 1

Arg Thr Leu Leu Val Asn Leu Asp Ser Asp Asp Val Lys Pro Glu Gly
 1               5                  10                  15

Gly Asp Asn Leu Gln
            20

<210> SEQ ID NO 2
<211> LENGTH: 20
<212> TYPE: PRT
<213> ORGANISM: Solanum tuberosum

<400> SEQUENCE: 2

Arg Leu Ser Ser Ala Gly Ile Thr His Val His Leu Leu Pro Thr Tyr
 1               5                  10                  15

Gln Phe Ala Gly
            20

<210> SEQ ID NO 3
<211> LENGTH: 10
<212> TYPE: PRT
<213> ORGANISM: Solanum tuberosum

<400> SEQUENCE: 3

Gly Ser Glu Val Leu Met His Asp Gly Lys
 1               5                  10

<210> SEQ ID NO 4
<211> LENGTH: 14
<212> TYPE: PRT
<213> ORGANISM: Solanum tuberosum

<400> SEQUENCE: 4

Ser Pro Ser Glu Ala Asp Pro Val Glu Ile Val Gln Leu Lys
 1               5                  10

<210> SEQ ID NO 5
<211> LENGTH: 12
<212> TYPE: PRT
<213> ORGANISM: Solanum tuberosum

<400> SEQUENCE: 5

Asp Cys Ile Gln Val Gly Met Ala Ala Asn Asp Lys

<210> SEQ ID NO 6
<211> LENGTH: 10
<212> TYPE: PRT
<213> ORGANISM: Solanum tuberosum

<400> SEQUENCE: 6

Lys Leu Gln Leu His Pro Val Gln Met Asn
 1               5                  10

<210> SEQ ID NO 7
<211> LENGTH: 10
<212> TYPE: PRT
<213> ORGANISM: Solanum tuberosum

<400> SEQUENCE: 7

Glu Leu Asp Gly Val Val Trp Ser Ala Glu
 1               5                  10

<210> SEQ ID NO 8
<211> LENGTH: 10
<212> TYPE: PRT
<213> ORGANISM: Solanum tuberosum

<400> SEQUENCE: 8

Ser Leu Leu Asn Ser Leu Ser Thr Glu Lys
 1               5                  10

<210> SEQ ID NO 9
<211> LENGTH: 11
<212> TYPE: PRT
<213> ORGANISM: Solanum tuberosum

<400> SEQUENCE: 9

Ala Asn Val Glu Arg Met Leu Thr Val Ser Lys
 1               5                  10

<210> SEQ ID NO 10
<211> LENGTH: 15
<212> TYPE: PRT
<213> ORGANISM: Solanum tuberosum

<400> SEQUENCE: 10

Leu Glu Gln Thr Asn Tyr Gly Leu Pro Gln Gln Val Ile Glu Lys
 1               5                  10                  15

<210> SEQ ID NO 11
<211> LENGTH: 9
<212> TYPE: PRT
<213> ORGANISM: Solanum tuberosum

<400> SEQUENCE: 11

Tyr Gly Leu Pro Val Gln Val Phe Glu
 1               5

<210> SEQ ID NO 12
<211> LENGTH: 13
<212> TYPE: PRT
<213> ORGANISM: Solanum tuberosum

<400> SEQUENCE: 12

Arg Thr Leu Leu Val Asn Leu Asn Ser Asp Asp Val Lys
 1               5                  10

<210> SEQ ID NO 13
<211> LENGTH: 9
<212> TYPE: PRT
<213> ORGANISM: Spinacia oleracea

<400> SEQUENCE: 13

Gln Pro Ile Glu Thr Ile Asn Tyr Val
 1               5

<210> SEQ ID NO 14
<211> LENGTH: 7
<212> TYPE: PRT
<213> ORGANISM: Spinacia oleracea

<400> SEQUENCE: 14

Asn Ile Asp Gly Val Glu Gly
 1               5

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 15
atwgtytcra twggytgcat                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 16
aayatygatg gwgtggargg                                              20

<210> SEQ ID NO 17
<211> LENGTH: 3437
<212> TYPE: DNA
<213> ORGANISM: Spinacia oleracea
<220> FEATURE:
<221> NAME/KEY: CDS
<222> LOCATION: (201)..(3095)

<400> SEQUENCE: 17
aaaacattcc gattagcggc aaataacaaa ccccaaacaa actctaacca tgaaatctca       60 tcttttaac atcattttc atcgaaatct acgttctgta actaattttc ccactttaca      120
gcatcattct tcatctgctc aactgaattt tctgcttaaa ccgccatagc caaaaacttc      180
aacctcacat tatcgctcta atg tct tca cta tat aac ccc att gct ctt gct     233
                        Met Ser Ser Leu Tyr Asn Pro Ile Ala Leu Ala
                         1               5                  10 tct agt ttc cat cac cat tat cct aat ctt cgt ttt cta ccc ttt aat       281
Ser Ser Phe His His His Tyr Pro Asn Leu Arg Phe Leu Pro Phe Asn
             15                  20                  25 ttc aat ttt att acc aaa tta ccc gtt tct aat tcc ttt gct att ggg       329
Phe Asn Phe Ile Thr Lys Leu Pro Val Ser Asn Ser Phe Ala Ile Gly
         30                  35                  40 tct agt tct aga agc ttc cat tca tcg cca ttg aag aag gat tct tct       377
Ser Ser Ser Arg Ser Phe His Ser Ser Pro Leu Lys Lys Asp Ser Ser -continued

```
             45                      50                      55
tgc ttt tgt tgt tcc atg gct gtc gaa gtt ggt tct gct tct tct gtt      425
Cys Phe Cys Cys Ser Met Ala Val Glu Val Gly Ser Ala Ser Ser Val
 60                      65                      70                      75 tct cag agt gaa ttg caa gga agt ttg aat agt tgt aga gcg tat tgg      473
Ser Gln Ser Glu Leu Gln Gly Ser Leu Asn Ser Cys Arg Ala Tyr Trp
                 80                      85                      90 cct agc aag tat aca ttt gcc tgg aat gtt gat att ggt aat ggt tca      521
Pro Ser Lys Tyr Thr Phe Ala Trp Asn Val Asp Ile Gly Asn Gly Ser
             95                     100                     105 tat tac tta ttt gca agt aaa act gct gcc cta aag ttt aca gat gct      569
Tyr Tyr Leu Phe Ala Ser Lys Thr Ala Ala Leu Lys Phe Thr Asp Ala
         110                     115                     120 ggg ata gaa gga tac gac gtg aaa atc aag ctt gac aag gac caa ggg      617
Gly Ile Glu Gly Tyr Asp Val Lys Ile Lys Leu Asp Lys Asp Gln Gly
     125                     130                     135 gga ttg cca gca aat gtc act gaa aaa ttt cct cat att aga ggt tac      665
Gly Leu Pro Ala Asn Val Thr Glu Lys Phe Pro His Ile Arg Gly Tyr
140                     145                     150                     155 tcg gcc ttt aaa gct cca gcc aca ctg gat gtt gat agt ctg ctg aag      713
Ser Ala Phe Lys Ala Pro Ala Thr Leu Asp Val Asp Ser Leu Leu Lys
                    160                     165                     170 tgt caa ctt gca gtt gct gct ttc agt gct gac ggg gct tgc aga aat      761
Cys Gln Leu Ala Val Ala Ala Phe Ser Ala Asp Gly Ala Cys Arg Asn
                175                     180                     185 gct act ggt ttg cag ttg cct ggc gtt att gat gag ttg tat tca tat      809
Ala Thr Gly Leu Gln Leu Pro Gly Val Ile Asp Glu Leu Tyr Ser Tyr
            190                     195                     200 gat ggc cct ctg ggt gct gtt ttc tca gaa aac acc ata tca ctg tac      857
Asp Gly Pro Leu Gly Ala Val Phe Ser Glu Asn Thr Ile Ser Leu Tyr
        205                     210                     215 cta tgg gct cct act gct caa gct gtt tct gcc agc ata ttt aag gat      905
Leu Trp Ala Pro Thr Ala Gln Ala Val Ser Ala Ser Ile Phe Lys Asp
220                     225                     230                     235 cca tca ggt ggt gaa cca tta caa acc gtc cag ctt ata gag tca aat      953
Pro Ser Gly Gly Glu Pro Leu Gln Thr Val Gln Leu Ile Glu Ser Asn
                    240                     245                     250 ggt gtt tgg agc gct gtg ggg cca aga acc tgg gag ggg tgt tat tat     1001
Gly Val Trp Ser Ala Val Gly Pro Arg Thr Trp Glu Gly Cys Tyr Tyr
                255                     260                     265 gtt tat gaa atc act gtc tat cac cat agc acc ttg aga att gaa aaa     1049
Val Tyr Glu Ile Thr Val Tyr His His Ser Thr Leu Arg Ile Glu Lys
            270                     275                     280 agc ttt gct att gat cca tat gcc aga ggg att tca gct gat gta aag     1097
Ser Phe Ala Ile Asp Pro Tyr Ala Arg Gly Ile Ser Ala Asp Val Lys
        285                     290                     295 cga aca tta ttg gct gac tta agc tct gaa act cta aag cct gaa gga     1145
Arg Thr Leu Leu Ala Asp Leu Ser Ser Glu Thr Leu Lys Pro Glu Gly
300                     305                     310                     315 tgg gaa aat ctt gct gat gaa aaa cct cat ctt ctt tct cca tct gac     1193
Trp Glu Asn Leu Ala Asp Glu Lys Pro His Leu Leu Ser Pro Ser Asp
                    320                     325                     330 atc agt ctc tat gag ctg cat ata aga gat ttc agt gct tat gac ctc     1241
Ile Ser Leu Tyr Glu Leu His Ile Arg Asp Phe Ser Ala Tyr Asp Leu
                335                     340                     345 act gtg cac cct gac ctt cgt ggt gga tat ctt gct ttc act tca cag     1289
Thr Val His Pro Asp Leu Arg Gly Gly Tyr Leu Ala Phe Thr Ser Gln
            350                     355                     360 gac tca gct ggt gtt aat cat ttg gaa aag tta tct gct gct ggt ctt     1337
```

```
Asp Ser Ala Gly Val Asn His Leu Glu Lys Leu Ser Ala Ala Gly Leu
    365                 370                 375 act cac gtt cat ctg ctg cca agc ttc cag ttt gct gaa gtt gat gat        1385
Thr His Val His Leu Leu Pro Ser Phe Gln Phe Ala Glu Val Asp Asp
380                 385                 390                 395 gac aaa aag aag tgg aaa ttt gtt gat act aag agg ttt gaa aca cta        1433
Asp Lys Lys Lys Trp Lys Phe Val Asp Thr Lys Arg Phe Glu Thr Leu
                400                 405                 410 cca cct gat tca gaa gag caa caa gct caa ata act gcc atc cga gat        1481
Pro Pro Asp Ser Glu Glu Gln Gln Ala Gln Ile Thr Ala Ile Arg Asp
            415                 420                 425 gaa gat gga tat aac tgg ggg tat aat cct gtt ttg tgg gga act cct        1529
Glu Asp Gly Tyr Asn Trp Gly Tyr Asn Pro Val Leu Trp Gly Thr Pro
        430                 435                 440 aag gga agc tat gca aca gat cca aat ggt cca tgc cgt ata att gag        1577
Lys Gly Ser Tyr Ala Thr Asp Pro Asn Gly Pro Cys Arg Ile Ile Glu
    445                 450                 455 ttc aga aag atg gtc cag gcg cta aat cgt att ggt ctt cgc gta gtt        1625
Phe Arg Lys Met Val Gln Ala Leu Asn Arg Ile Gly Leu Arg Val Val
460                 465                 470                 475 ttg gat gtt gtt tat aac cat tta aat agc agt ggg ccc tcc gat gat        1673
Leu Asp Val Val Tyr Asn His Leu Asn Ser Ser Gly Pro Ser Asp Asp
                480                 485                 490 aat tct gtc ctg gac aag att gtt cca ggt tac tac tta aga aga gat        1721
Asn Ser Val Leu Asp Lys Ile Val Pro Gly Tyr Tyr Leu Arg Arg Asp
            495                 500                 505 aat gat ggt gct att gaa aat agc aca tgt gtg aat gac aca gct agc        1769
Asn Asp Gly Ala Ile Glu Asn Ser Thr Cys Val Asn Asp Thr Ala Ser
        510                 515                 520 gag cat ttt atg gtt gaa cgc ctg att ttg gat gat cta aaa cat tgg        1817
Glu His Phe Met Val Glu Arg Leu Ile Leu Asp Asp Leu Lys His Trp
    525                 530                 535 gcg gtg aat tat aag gtt gat ggt ttc aga ttt gat ctt atg ggc cac        1865
Ala Val Asn Tyr Lys Val Asp Gly Phe Arg Phe Asp Leu Met Gly His
540                 545                 550                 555 ata atg aaa cat acg atg gtg aaa gcg aca aat atg ctc caa ggc ctg        1913
Ile Met Lys His Thr Met Val Lys Ala Thr Asn Met Leu Gln Gly Leu
                560                 565                 570 tca aaa aac ata gat ggt gta gag ggt tca agc att tat tta tat ggt        1961
Ser Lys Asn Ile Asp Gly Val Glu Gly Ser Ser Ile Tyr Leu Tyr Gly
            575                 580                 585 gaa gga tgg gac ttt ggc gag gtg gca aat aat gca cgt gga gta aat        2009
Glu Gly Trp Asp Phe Gly Glu Val Ala Asn Asn Ala Arg Gly Val Asn
        590                 595                 600 gca tct caa ctg aat ctt gga gga aca gga att gga agt ttt aat gat        2057
Ala Ser Gln Leu Asn Leu Gly Gly Thr Gly Ile Gly Ser Phe Asn Asp
    605                 610                 615 cgg att cga gat gca gtg ctt ggt ggg ggg cct ttt ggt ccc cct ctt        2105
Arg Ile Arg Asp Ala Val Leu Gly Gly Gly Pro Phe Gly Pro Pro Leu
620                 625                 630                 635 cag caa ggt tac gtg act ggt tta tct tta cag cct aat gat cat gac        2153
Gln Gln Gly Tyr Val Thr Gly Leu Ser Leu Gln Pro Asn Asp His Asp
                640                 645                 650 cat agc ggt aaa gcc aat gca gac cgt atg ctt gct gtg gca aaa gat        2201
His Ser Gly Lys Ala Asn Ala Asp Arg Met Leu Ala Val Ala Lys Asp
            655                 660                 665 cat atc cag gtt ggg atg gct gga aac ttg aga gac tac att ctg aca        2249
His Ile Gln Val Gly Met Ala Gly Asn Leu Arg Asp Tyr Ile Leu Thr
        670                 675                 680
```

```
aac tgt gat gga aaa cag gta aaa ggc tca gaa gtt tat acc tat ggg    2297
Asn Cys Asp Gly Lys Gln Val Lys Gly Ser Glu Val Tyr Thr Tyr Gly
685                 690                 695 gga acg ccg gtt ggg tat gct atg cag ccg ata gaa act atc aac tat    2345
Gly Thr Pro Val Gly Tyr Ala Met Gln Pro Ile Glu Thr Ile Asn Tyr
700                 705                 710                 715 gtc tca gct cat gac aac gaa act ctt ttc gat att gtc agt ttg aag    2393
Val Ser Ala His Asp Asn Glu Thr Leu Phe Asp Ile Val Ser Leu Lys
            720                 725                 730 act cct acc tac att acg gtg gat gag aga tgt agg gta aat cat tta    2441
Thr Pro Thr Tyr Ile Thr Val Asp Glu Arg Cys Arg Val Asn His Leu
735                 740                 745 gct acg agt att cta gca ctt tcc cag gga ata ccc ttt ttc cat gct    2489
Ala Thr Ser Ile Leu Ala Leu Ser Gln Gly Ile Pro Phe Phe His Ala
    750                 755                 760 ggt gat gag ttg cta cgt tca aag tcc ctt gac cgt gat tct tat aac    2537
Gly Asp Glu Leu Leu Arg Ser Lys Ser Leu Asp Arg Asp Ser Tyr Asn
765                 770                 775 tct ggt gat tgg ttt aac aga tta gac ttc agc tat aac tcc aac aat    2585
Ser Gly Asp Trp Phe Asn Arg Leu Asp Phe Ser Tyr Asn Ser Asn Asn
780                 785                 790                 795 tgg ggt gtt ggt ctc cct ccc aag gat cac aat gag agc aat tgg cca    2633
Trp Gly Val Gly Leu Pro Pro Lys Asp His Asn Glu Ser Asn Trp Pro
                800                 805                 810 tta atc aag aaa aga ttg gca aat ccg tcc tac aag cct gac aag aat    2681
Leu Ile Lys Lys Arg Leu Ala Asn Pro Ser Tyr Lys Pro Asp Lys Asn
            815                 820                 825 cac att att gct gct gtt gaa aat ttc acc aat ttg ttg caa att aga    2729
His Ile Ile Ala Ala Val Glu Asn Phe Thr Asn Leu Leu Gln Ile Arg
830                 835                 840 tac tct tct cca cta ttc cgt tta aga agt gca aag gat att gag gat    2777
Tyr Ser Ser Pro Leu Phe Arg Leu Arg Ser Ala Lys Asp Ile Glu Asp
    845                 850                 855 cga gta cga ttc cac aat aat gtt cca tct tgg att cct ggg ctt ata    2825
Arg Val Arg Phe His Asn Asn Val Pro Ser Trp Ile Pro Gly Leu Ile
860                 865                 870                 875 gct atg agc att gaa gat ggt cat gcg gga gcc cct ggc ttg tca cag    2873
Ala Met Ser Ile Glu Asp Gly His Ala Gly Ala Pro Gly Leu Ser Gln
                880                 885                 890 ata gat ccc aag ttc cag tac att gtt gta ata atc aat gtt cag cct    2921
Ile Asp Pro Lys Phe Gln Tyr Ile Val Val Ile Ile Asn Val Gln Pro
            895                 900                 905 act gaa acc aaa ttt gtt aac cca gat ctg cga gct aaa tcc cta cag    2969
Thr Glu Thr Lys Phe Val Asn Pro Asp Leu Arg Ala Lys Ser Leu Gln
910                 915                 920 ctg cat cca gta cag tca aca tca ggg gac acg gtt gtt aag gaa tca    3017
Leu His Pro Val Gln Ser Thr Ser Gly Asp Thr Val Val Lys Glu Ser
    925                 930                 935 aag tat gag cct tct act gga tgc ttt act ata cct cct aaa tca act    3065
Lys Tyr Glu Pro Ser Thr Gly Cys Phe Thr Ile Pro Pro Lys Ser Thr
940                 945                 950                 955 gca gtg ttc gtt gag cca cgg cat gtt taa gctgaagttg aagggtctgt      3115
Ala Val Phe Val Glu Pro Arg His Val
                960                 965 ccaagacggc gaccgcatgt ggttgtcagt aagtggagtt actttctgca tattacacgg  3175
ttcaatacaa ataaataacg tctgctaccg cagcgagctg aggtctcaca gaataagtta  3235
caaaaaagtt agcagttata tttcataagt tcatagttca gctgaataag aaccaccaaa  3295
atcttacgtt gtacttgtag cagtgctttt gtcacgcata ataatcagt tgcttgttaa   3355
```

```
ccatacatcc gatatgaatg aataatttttt tttttttttaa aaaaaaaaaa aaaaaaaaaa    3415
aaaaaaaaaa aaaaaaaaaa aa                                              3437
```

<210> SEQ ID NO 18
<211> LENGTH: 964
<212> TYPE: PRT
<213> ORGANISM: Spinacia oleracea

<400> SEQUENCE: 18

```
Met Ser Ser Leu Tyr Asn Pro Ile Ala Leu Ala Ser Ser Phe His His
  1               5                  10                  15

His Tyr Pro Asn Leu Arg Phe Leu Pro Phe Asn Phe Asn Phe Ile Thr
             20                  25                  30

Lys Leu Pro Val Ser Asn Ser Phe Ala Ile Gly Ser Ser Ser Arg Ser
         35                  40                  45

Phe His Ser Ser Pro Leu Lys Lys Asp Ser Ser Cys Phe Cys Cys Ser
     50                  55                  60

Met Ala Val Glu Val Gly Ser Ala Ser Ser Val Ser Gln Ser Glu Leu
 65                  70                  75                  80

Gln Gly Ser Leu Asn Ser Cys Arg Ala Tyr Trp Pro Ser Lys Tyr Thr
                 85                  90                  95

Phe Ala Trp Asn Val Asp Ile Gly Asn Gly Ser Tyr Tyr Leu Phe Ala
            100                 105                 110

Ser Lys Thr Ala Ala Leu Lys Phe Thr Asp Ala Gly Ile Glu Gly Tyr
        115                 120                 125

Asp Val Lys Ile Lys Leu Asp Lys Asp Gln Gly Gly Leu Pro Ala Asn
    130                 135                 140

Val Thr Glu Lys Phe Pro His Ile Arg Gly Tyr Ser Ala Phe Lys Ala
145                 150                 155                 160

Pro Ala Thr Leu Asp Val Asp Ser Leu Leu Lys Cys Gln Leu Ala Val
                165                 170                 175

Ala Ala Phe Ser Ala Asp Gly Ala Cys Arg Asn Ala Thr Gly Leu Gln
            180                 185                 190

Leu Pro Gly Val Ile Asp Glu Leu Tyr Ser Tyr Asp Gly Pro Leu Gly
        195                 200                 205

Ala Val Phe Ser Glu Asn Thr Ile Ser Leu Tyr Leu Trp Ala Pro Thr
    210                 215                 220

Ala Gln Ala Val Ser Ala Ser Ile Phe Lys Asp Pro Ser Gly Gly Glu
225                 230                 235                 240

Pro Leu Gln Thr Val Gln Leu Ile Glu Ser Asn Gly Val Trp Ser Ala
                245                 250                 255

Val Gly Pro Arg Thr Trp Glu Gly Cys Tyr Tyr Val Tyr Glu Ile Thr
            260                 265                 270

Val Tyr His His Ser Thr Leu Arg Ile Glu Lys Ser Phe Ala Ile Asp
        275                 280                 285

Pro Tyr Ala Arg Gly Ile Ser Ala Asp Val Lys Arg Thr Leu Leu Ala
    290                 295                 300

Asp Leu Ser Ser Glu Thr Leu Lys Pro Glu Gly Trp Glu Asn Leu Ala
305                 310                 315                 320

Asp Glu Lys Pro His Leu Leu Ser Pro Ser Asp Ile Ser Leu Tyr Glu
                325                 330                 335

Leu His Ile Arg Asp Phe Ser Ala Tyr Asp Leu Thr Val His Pro Asp
            340                 345                 350
```

```
Leu Arg Gly Gly Tyr Leu Ala Phe Thr Ser Gln Asp Ser Ala Gly Val
        355                 360                 365

Asn His Leu Glu Lys Leu Ser Ala Ala Gly Leu Thr His Val His Leu
    370                 375                 380

Leu Pro Ser Phe Gln Phe Ala Glu Val Asp Asp Lys Lys Lys Trp
385                 390                 395                 400

Lys Phe Val Asp Thr Lys Arg Phe Glu Thr Leu Pro Pro Asp Ser Glu
                405                 410                 415

Glu Gln Gln Ala Gln Ile Thr Ala Ile Arg Asp Glu Asp Gly Tyr Asn
            420                 425                 430

Trp Gly Tyr Asn Pro Val Leu Trp Gly Thr Pro Lys Gly Ser Tyr Ala
        435                 440                 445

Thr Asp Pro Asn Gly Pro Cys Arg Ile Ile Glu Phe Arg Lys Met Val
    450                 455                 460

Gln Ala Leu Asn Arg Ile Gly Leu Arg Val Val Leu Asp Val Val Tyr
465                 470                 475                 480

Asn His Leu Asn Ser Ser Gly Pro Ser Asp Asp Asn Ser Val Leu Asp
                485                 490                 495

Lys Ile Val Pro Gly Tyr Tyr Leu Arg Arg Asp Asn Asp Gly Ala Ile
            500                 505                 510

Glu Asn Ser Thr Cys Val Asn Asp Thr Ala Ser Glu His Phe Met Val
        515                 520                 525

Glu Arg Leu Ile Leu Asp Asp Leu Lys His Trp Ala Val Asn Tyr Lys
    530                 535                 540

Val Asp Gly Phe Arg Phe Asp Leu Met Gly His Ile Met Lys His Thr
545                 550                 555                 560

Met Val Lys Ala Thr Asn Met Leu Gln Gly Leu Ser Lys Asn Ile Asp
                565                 570                 575

Gly Val Glu Gly Ser Ser Ile Tyr Leu Tyr Gly Glu Gly Trp Asp Phe
            580                 585                 590

Gly Glu Val Ala Asn Asn Ala Arg Gly Val Asn Ala Ser Gln Leu Asn
        595                 600                 605

Leu Gly Gly Thr Gly Ile Gly Ser Phe Asn Asp Arg Ile Arg Asp Ala
    610                 615                 620

Val Leu Gly Gly Gly Pro Phe Gly Pro Pro Leu Gln Gln Gly Tyr Val
625                 630                 635                 640

Thr Gly Leu Ser Leu Gln Pro Asn Asp His Asp His Ser Gly Lys Ala
                645                 650                 655

Asn Ala Asp Arg Met Leu Ala Val Ala Lys Asp His Ile Gln Val Gly
            660                 665                 670

Met Ala Gly Asn Leu Arg Asp Tyr Ile Leu Thr Asn Cys Asp Gly Lys
        675                 680                 685

Gln Val Lys Gly Ser Glu Val Tyr Thr Tyr Gly Gly Thr Pro Val Gly
    690                 695                 700

Tyr Ala Met Gln Pro Ile Glu Thr Ile Asn Tyr Val Ser Ala His Asp
705                 710                 715                 720

Asn Glu Thr Leu Phe Asp Ile Val Ser Leu Lys Thr Pro Thr Tyr Ile
                725                 730                 735

Thr Val Asp Glu Arg Cys Arg Val Asn His Leu Ala Thr Ser Ile Leu
            740                 745                 750

Ala Leu Ser Gln Gly Ile Pro Phe Phe His Ala Gly Asp Glu Leu Leu
        755                 760                 765

Arg Ser Lys Ser Leu Asp Arg Asp Ser Tyr Asn Ser Gly Asp Trp Phe
```

-continued

```
              770                 775                 780
Asn Arg Leu Asp Phe Ser Tyr Asn Ser Asn Asn Trp Gly Val Gly Leu
785                 790                 795                 800

Pro Pro Lys Asp His Asn Glu Ser Asn Trp Pro Leu Ile Lys Lys Arg
                805                 810                 815

Leu Ala Asn Pro Ser Tyr Lys Pro Asp Lys Asn His Ile Ile Ala Ala
                820                 825                 830

Val Glu Asn Phe Thr Asn Leu Leu Gln Ile Arg Tyr Ser Ser Pro Leu
                835                 840                 845

Phe Arg Leu Arg Ser Ala Lys Asp Ile Glu Asp Arg Val Arg Phe His
850                 855                 860

Asn Asn Val Pro Ser Trp Ile Pro Gly Leu Ile Ala Met Ser Ile Glu
865                 870                 875                 880

Asp Gly His Ala Gly Ala Pro Gly Leu Ser Gln Ile Asp Pro Lys Phe
                885                 890                 895

Gln Tyr Ile Val Val Ile Ile Asn Val Gln Pro Thr Glu Thr Lys Phe
                900                 905                 910

Val Asn Pro Asp Leu Arg Ala Lys Ser Leu Gln Leu His Pro Val Gln
                915                 920                 925

Ser Thr Ser Gly Asp Thr Val Val Lys Glu Ser Lys Tyr Glu Pro Ser
                930                 935                 940

Thr Gly Cys Phe Thr Ile Pro Pro Lys Ser Thr Ala Val Phe Val Glu
945                 950                 955                 960

Pro Arg His Val
```

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 19
ccytcnggyt tnacrtcrtc                                               20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 20
gcggccatgc cgacytgdat                                               20

<210> SEQ ID NO 21
<211> LENGTH: 43
<212> TYPE: DNA
<213> ORGANISM: Artificial Sequence
<220> FEATURE:
<223> OTHER INFORMATION: Description of Artificial Sequence: man-made PCR
      primer

<400> SEQUENCE: 21
aaggtaccgg atcctctgct gatggcaagt ggacattatt agt                     43

<210> SEQ ID NO 22
<211> LENGTH: 41

<210> SEQ ID NO 22
<211> LENGTH: 41
<212> TYPE: DNA
<213> ORGANISM: Artificial Sequence
<220> FEATURE:
<223> OTHER INFORMATION: Description of Artificial Sequence: man-made PCR primer

<400> SEQUENCE: 22
ttaagcccgg gcgatacgac aaggaccatt tgcattacca g          41

<210> SEQ ID NO 23
<211> LENGTH: 492
<212> TYPE: DNA
<213> ORGANISM: Solanum tuberosum
<220> FEATURE:
<221> NAME/KEY: CDS
<222> LOCATION: (1)..(492)

<400> SEQUENCE: 23

```
tct gct gat ggc aag tgg aca tta tta gtt aat ctt gat tct gat gat    48
Ser Ala Asp Gly Lys Trp Thr Leu Leu Val Asn Leu Asp Ser Asp Asp
 1               5                  10                  15 gta aaa cct gaa ggc tgg gat aat cta caa gac gtg aag cca aat ctt    96
Val Lys Pro Glu Gly Trp Asp Asn Leu Gln Asp Val Lys Pro Asn Leu
             20                  25                  30 ctt tcc ttt tct gat gtc agc atc tat gag ctg cat gtt aga gat ttc   144
Leu Ser Phe Ser Asp Val Ser Ile Tyr Glu Leu His Val Arg Asp Phe
         35                  40                  45 act gcc agt gac cct act gtg tct cat gaa ttt cag gcc ggt tat ctc   192
Thr Ala Ser Asp Pro Thr Val Ser His Glu Phe Gln Ala Gly Tyr Leu
     50                  55                  60 gcc cct tcc acg tcg cag gca tca gct ggt gtc caa cat ttg aaa aga   240
Ala Pro Ser Thr Ser Gln Ala Ser Ala Gly Val Gln His Leu Lys Arg
 65                  70                  75                  80 tta tca agt gct ggt atc act cat gtc cac ctg tgg cca acc tat caa   288
Leu Ser Ser Ala Gly Ile Thr His Val His Leu Trp Pro Thr Tyr Gln
                 85                  90                  95 ttt gct ggt gtc gaa gat gag aaa cat aaa tgg aag tat aca gat atc   336
Phe Ala Gly Val Glu Asp Glu Lys His Lys Trp Lys Tyr Thr Asp Ile
            100                 105                 110 gag aaa ctc aac tct ttt cca cca gat tct gag gag cag cag gct ctt   384
Glu Lys Leu Asn Ser Phe Pro Pro Asp Ser Glu Glu Gln Gln Ala Leu
        115                 120                 125 atc aca gcc atc caa gat gaa gat ggc tat aat tgg ggg tat aat cct   432
Ile Thr Ala Ile Gln Asp Glu Asp Gly Tyr Asn Trp Gly Tyr Asn Pro
    130                 135                 140 gtt ctc tgg gga gtt cca aag gga agc tat gct ggt aat gca aat ggt   480
Val Leu Trp Gly Val Pro Lys Gly Ser Tyr Ala Gly Asn Ala Asn Gly
145                 150                 155                 160 cct tgt cgt atc                                                   492
Pro Cys Arg Ile
```

<210> SEQ ID NO 24
<211> LENGTH: 164
<212> TYPE: PRT
<213> ORGANISM: Solanum tuberosum

<400> SEQUENCE: 24

```
Ser Ala Asp Gly Lys Trp Thr Leu Leu Val Asn Leu Asp Ser Asp Asp
 1               5                  10                  15

Val Lys Pro Glu Gly Trp Asp Asn Leu Gln Asp Val Lys Pro Asn Leu
             20                  25                  30

Leu Ser Phe Ser Asp Val Ser Ile Tyr Glu Leu His Val Arg Asp Phe
```

-continued

```
                     35                  40                  45
Thr Ala Ser Asp Pro Thr Val Ser His Glu Phe Gln Ala Gly Tyr Leu
         50                  55                  60

Ala Pro Ser Thr Ser Gln Ala Ser Ala Gly Val Gln His Leu Lys Arg
 65                  70                  75                  80

Leu Ser Ser Ala Gly Ile Thr His Val His Leu Trp Pro Thr Tyr Gln
                 85                  90                  95

Phe Ala Gly Val Glu Asp Glu Lys His Lys Trp Lys Tyr Thr Asp Ile
             100                 105                 110

Glu Lys Leu Asn Ser Phe Pro Pro Asp Ser Glu Glu Gln Gln Ala Leu
         115                 120                 125

Ile Thr Ala Ile Gln Asp Glu Asp Gly Tyr Asn Trp Gly Tyr Asn Pro
         130                 135                 140

Val Leu Trp Gly Val Pro Lys Gly Ser Tyr Ala Gly Asn Ala Asn Gly
145                 150                 155                 160

Pro Cys Arg Ile
```